United States Patent [19]
Kozulic

[11] Patent Number: 5,840,877
[45] Date of Patent: Nov. 24, 1998

[54] ELECTROPHORESIS GELS OF ENHANCED SELECTIVITY

[75] Inventor: Branko Kozulic, Zurich, Switzerland

[73] Assignee: Guest Elchrom Scientific, Cham, Switzerland

[21] Appl. No.: 708,492

[22] Filed: Sep. 5, 1996

[51] Int. Cl.[6] .............................. C12N 15/10; C25B 7/00; C08F 20/56

[52] U.S. Cl. .......................... 536/25.4; 536/124; 526/304; 356/344; 204/456

[58] Field of Search .................................. 536/123.1, 124, 536/25.4; 526/304; 356/344; 204/456

[56] References Cited

U.S. PATENT DOCUMENTS

| | | | |
|---|---|---|---|
| 4,582,868 | 4/1986 | Ogawa et al. | |
| 4,963,243 | 10/1990 | Ogawa et al. | |
| 4,999,340 | 3/1991 | Hoffman et al. | 514/23 |
| 5,319,046 | 6/1994 | Kozulic et al. | 526/304 |

OTHER PUBLICATIONS

Andrew C. Peacock et al., "Molecular Weight Estimation and Separation of Ribonuclecic Acid by Electrophoresis in Agarose–Acrylamide Composite Gels*", *Biochemistry*, Feb. 1968, vol. 7, No. 2, 668–674.

Hans–Joachim Bode, "The Use of Liquid Polyacrylamide in Electrophoresis", *Analytical Biochemistry* (1977) 83, 204–210.

Paul M. Horowitz et al., "Electrophoresis of Proteins and Nucleic Acids on Acrylamide–Agarose Gels Lacking Covalent Crosslinking", *Analytical Biochemistry* (1984) 143, 333–340.

Hans–Joachim Bode, "SDS–Polyethyleneglycol Electrophoresis: A Possible Altenative to SDS–Polyacrylamide Gel Electrophoresis", *FEBS Letters*, May 1976, vol. 65, No. 1, 56–58.

Pier Giorgio Righetti et al., "'Laterally Aggregated' Polyacrylamide Gels for Electrophoresis", *Electrophoresis*, 1992, 13, 587–595.

D. Asnaghi et al., "Large–scale Microsegregation in Polyacrylamide Gels (Spinodal Gels)", *J. Chem. Phys.*, Jun. 22, 1995, 102(24), 9736–9742.

Pier Giorgio Richetti et al., "On The Limiting Pore Size of Hydrophilic Gels for Electrophoresis and Isoelectric Focusing", *Journal of Biochemical and Biophysical Methods*, 4 (1981) 347–363.

Cecilia Gelfi et al, "Polymerization Kinetics of Polyacrylamide Gels I. Effect of Different Cross–Linkers", *Electrophoresis*, 1981, 2, 213–219.

Baruch J. Davis, "Disc Electrophoresis–II Method and Application to Human Serum Proteins", *Annuals New York Academy of Sciences*, Jan. 1962, 404–427.

Pier Giorgio Righetti, "Review of Matrices and Men", *Journal of Biochemical and Biophysical Methods*, 19 (1989), 1–20.

David Rodbard et al., "Unified Theory for Gel Electrophoresis and Gel Filtration", *Proceedings of the National Academy of Sciences*, Apr. 1970, 65, 4, 970–977.

Dietmar Tietz, "Evaluation of Mobility Data Obtained From Gel Electrophoresis: Strategies in the Computation of Particle and Gels Properties on the Basis of the Extended Ogston Model", *National Institutes of Health, Bethesda, MD, USA*, undated, pp. 110–168, 1988.

M. Wyckoff et al., "Polyacylamide Gel Electrophoresis in Sodium Dodecyl Sulfate–Containing Buffers Using Multiphasic Buffer Systems: Properties of the Stack, Valid $R_f$ Measurrement, and Optimized Proedure", *Analytical Biochemistry*, (1977), 78, 459–482.

Nancy C. Stellwagen, "Electophoresis of DNA in Agarose and Polyacrylamide Gels", *University of Iowa, Iowa City, IA, USA*, pp. 177–228, 1987.

Hana Kovarova et al., *Applied and Theoretical Electrophoresis*, "Two–dimensional electrophoretic study of normal colon mucosa and colorectal cancer", 1994, vol. 4, No. 3, 103–106.

Mirko Deml et al., *Applied and Theoretical Electrophoresis*, "Electrically controlled focusing of proteins and ampholytes between two modified electrolytes. Computer stimulation", 1994, vol. 4, No. 3, 107–115.

Branko Kozulic, *Applied and Theoretical Electrophresis*, "A model of gel electrophoresis", 1994, vol. 4, No. 3, 117–123.

Branko Kozulic, *Applied and Theoretical Electrophoresis*, "On the door–corridor model of gel electrophoresis. I. Equations describing the relationship between mobility and size of DNA fragments and protein–SDS complexes", 1994, vol. 4, No. 3, 125–136.

Branko Kozulic, *Applied and Theoretical Electrophoresis*, "On the door–corridor model of gel electrophoresis. II. Developments related to new gels, capillary gel electrophoresis and gel chromatography", 1994, vol. 4, No. 3, 137–148.

(List continued on next page.)

*Primary Examiner*—Gary L. Kunz
*Attorney, Agent, or Firm*—Lowe Hauptman Gopstein Gilman & Berner

[57] ABSTRACT

Electrophoresis gels of enhanced selectivity are produced by adding a preformed polymer to a polymerization solution containing at least one monomer and at least one cross-linker. The polymer must be of such a chemical composition and molecular weight that its presence during free-radical polymerization results in a new topology of gel polymers, so that under the influence of an electric field, such as during electrophoresis, the passage of long DNA molecules through the gel is retarded proportionally more than the passage of the short ones. The polymer needs to be added at specific ratio to the monomer and the cross-linker, and the enhanced selectivity is achievable only within a certain range of ratios of polymer(s), monomer(s) and cross linker(s). That range is dependent on all three essential gel components, the polymer, the monomer and the cross-linker. Some gels possessing enhanced selectivity were able to resolve one base pair differences between DNA fragments in the 100 bp range with the gel length of less than 10 cm.

90 Claims, 12 Drawing Sheets

OTHER PUBLICATIONS

Branko Kozulic, *Applied and Theoretical Electrophoresis,* "On the door–corridor model of gel electrophoresis. III. The gel constant and resistance, and the net charge, friction, diffusion and electrokinetic force of the migrating molecules", 1994, vol. 4, No. 3, 149–159.

Branko Kozulic, "Models of Gel Electrophoresis", *Analytical Biochemistry,* (1995), 231, 1–12.

Eric Brassard et al., "Pulsed Field Sequencing Gel Electrophoresis", *Electrophoresis,* (1992), 13, 529–535.

Levy Ulanovsky et al., "DNA Trapping Electrophoresis", *Letters to Nature,* Jan. 11, 1990, vol. 343, pp. 190–192.

Claude Desruisseaux et al., "Pulsed–field Trapping Electrophoresis: A Computer Simulation Study", *Electrophoresis,* 1996, 17, 623–632.

Marcella Chiari et al., "Electrophoretic Separation of Biopolymers in a Matrix of Polyacrylamide Covalently Linked to Agarose", *Electrophoresis,* 1996, 17, 473–478.

Annelise E. Barron et al., "The Effects of Polymer Properties on DNA Separations by Capillary Electrophoresis in Uncross–linked Polymer Solutions", *Electrophoresis,* 1996, 17, 744–757.

Hans–Joachim Bode, "A Viscosity Model of Polyacrylamide Gel Electrophoresis", pp. 512–528, 1979.

Lenore L. Cai, et al., "Nanorheology of Polymers", *Reviews,* Feb. 1996, vol. 4, No. 2, 47–51.

Douglas M. Gersten et al., "Polyacrylamide Gel Electrophoresis in Vertical, Inverse and Double–crossing Gradients of Soluble Polymers", *Electrophoresis,* 1992, 13, 282–286.

Jan Pospichal et al., "Free Mobility Determination by Electrophoresis in Polyacrylamide Containing Agarose at a Nonrestrictive Concentration", *Electrophoresis,* 1991, 12, 247–253.

Diane L. Holmes et al., "Estimation of Polyacrylamide Gel Pore Size from Ferguson Plots of Linear DNA Fragments II. Comparison of Gels with Different Crosslinker Concentrations, Added Agarose and Added Linear Polyacrylamide", *Electrophoresis,* 1991, 12, 612–619.

H.J. Bode, "Partitioning and Electrophoresis in Flexible Polymer Networks", *Electrophoresis,* 1979, 39–52.

ELECTROPHORESIS GELS OF ENHANCED SELECTIVITY

BACKGROUND OF THE INVENTION

In gel electrophoresis, a mixture of charged species is resolved into its components owing to different mobilities of these species in an imposed electric field. The mobilities largely depend on the gel used and on the characteristics of ions themselves, including net surface charge, size and shape. Gel electrophoresis is currently employed mostly for the separation of biological macromolecules, such as proteins, nucleic acids and their derivatives. The gels may be composed of natural or synthetic polymers. Regardless of the materials from which they are made, the gels can be run positioned vertically or horizontally in appropriate electrophoretic chambers, or used in the capillary format. While each particular format has its advantages and disadvantages, the major determinant of a successful separation is the gel itself.

In recent years, many new gel materials have been described in scientific literature or disclosed in patents. They include polymers made from novel monomers, or combinations of monomers and cross-linkers, or modified natural polymers. Some of these new gels made of novel materials showed substantially different properties, leading to important improvements of electrophoretic separations.

There has been introduced a new synthetic matrix for the analysis of proteins and nucleic acids (U.S. Pat. No. 5,319,046). The matrix is based on an acrylic monomer, N-acryloyl-tris(hydroxymethyl)aminomethane (NAT). The poly(NAT) gels are more hydrophilic than the polyacrylamide gels that had previously been used, and they give improved resolution of large molecules. A series of even more hydrophilic polymers, made from novel monomers, and gels was also disclosed (U.S. Pat. Nos. 5,185,466 and 5,202,007). These gels were particularly suitable for separating DNA restriction fragments and proteins. Another gel type was disclosed in U.S. Pat. No. 5,371,208. These gels consisted of linear polymers cross-linked with a cross-linker which reacted with hydroxyl groups of the polymers to give ether cross links.

Gels for electrophoresis can be prepared by free radical polymerization, by thermally induced gelation, and by a cross-linking reaction taking place simultaneously with gelation. Each one of the three processes is currently being used for the production of precast gels for electrophoresis. Given the large number of existing starting materials, a great variety of gels can be produced by using different combinations of these materials. There is an additional possibility of varying the properties of gels suitable for use in electrophoresis, consisting of introducing an additive into a formed gel or into a gelling solution. The additive is chosen such that it improves a particular property of the gel to which it is added. For example, it is known that mechanical properties of polyacrylamide gels of low concentrations (3–5%) are poor. The mechanical stability can be improved when such gels are polymerized in the presence of agarose, since agarose gels possess excellent mechanical stability at low concentrations. Such composite gels were described in reference 1. The elasticity of polyacrylamide gels can be improved by adding a separate, preformed polymer into the polymerization solution, and such gels are commercially known under the trade name Duracryl (Oxford Glycosystems). The exact nature of the additive polymer has not been disclosed. Other additives which have been used with polyacrylamide gels include low molecular weight polyols (U.S. Pat. No. 5,159,049).

Additives have been used in combination with agarose gels as well. Agarose gels have inferior optical properties compared to polyacrylamide gels. This drawback can be partially corrected by adding another polysaccharides into an agarose solution prior to its gelation (U.S. Pat. No. 5,230,832). Moreover, agarose gels containing liquid polyacrylamide are also known, and in these gels the agarose provided mechanical stability whereas the polyacrylamide served as sieving medium (references 2 and 3). Another example includes the addition of polyethylene glycol (PEG) into a pre-formed gel, such as a cellulose acetate gel. In this combination the cellulose acetate served as the stabilizing medium whereas the PEG was the sieving medium (reference 4). A branched polysaccharide incorporated into a cross-linked linear polysaccharide gel (U.S. Pat. No. 5,371,208) can be considered as an additive.

In U.S. Pat. No. 5,319,046 it was disclosed that poly (NAT) gels may additionally contain acrylamide or agarose. The latter can be regarded as an additive, but not the former. When two acrylic monomers are present during gel polymerization, they copolymerize and therefore a single polymer chain results which contains units derived from each of the two monomers. On the other hand, the relation is more complex between the polymers formed by polymerization in the presence of an additive, since in some instances the newly formed polymer and the preformed additive will become covalently linked by a chain transfer reaction during free-radical polymerization. This can occur even when the additive contains no vinyl groups. On the other hand, in thermally induced gels, a preformed polymeric additive is not expected to become covalently bound to gel polymers. In both types of gels, those formed by free-radical polymerization or produced by thermally induced gelation, a polymeric additive may be intertwined with the gelled polymers so strongly that for all practical applications one may consider it as an integral part of the gel matrix. Alternatively, the additive may be only loosely associated with gel polymers, or it may just remain in the gel interstices, allowing easy diffusion out of the gel.

It is important to consider the influence of additives on electrophoretic mobilities of the molecules that were analyzed in the gels known in prior art. In low concentration polyacrylamide gels stabilized with agarose, the separation depended principally on the acrylamide component of the gel (reference 1). In the agarose-liquid polyacrylamide gels, agarose polymers were considered non-sieving, as the mobilities of the materials passing through the gels were a function of the polyacrylamide concentration (references 2 and 3). In polyacrylamide gels with improved elasticity due to an added polymer (Duracryl), according to the manufacturer the electrophoretic mobilities are equal to those found in plain polyacrylamide gels used for the same purpose, which is usually two-dimensional electrophoresis of proteins. Regarding additives introduced into pre-formed gels, some small molecular weight polyols changed mobilities of analyzed molecules whereas the others did not (U.S. Pat. No. 5,159,049). In the PEG-supplemented cellulose acetate gels, SDS-protein complexes could be resolved only in the presence of added PEG, that is, the pre-existing cellulose acetate matrix served only as stabilizing medium (reference 4).

Recently, several reports appeared on PEG-supplemented polyacrylamide gels (references 5 and 6). The addition of PEG to an acrylamide-N,N'-methylene-bis-acrylamide (Bis) solution prior to polymerization resulted in gels with surprisingly different properties. First, the optical properties of the gels were changed. That is the gels became strongly opaque. Second, electrophoretic mobilities were greatly altered, such that larger DNA molecules migrated much faster in these new gels. The increased DNA migration rates coincided thus with the higher opacity of the gels. The results appeared consistent with the formation of large pores due to lateral aggregation of polyacrylamide fibers (references 5 and 6). Opaque polyacrylamide gels, without additives, are formed when the concentration of Bis is increased above about 5% while the concentration of acrylamide plus Bis is kept constant (references 7 and 8). Herein the concentration of gel components is always expressed in weight per volume. The total gel concentration T and the cross-linker concentration C are defined as customary in the prior art, so that T relates to the sum of the monomer and cross-linker weight, and C denotes the percentage of the cross-linker relative to T. It is known that in opaque polyacrylamide gels formed at high Bis concentrations, macromolecules migrate at higher rates, and such gels are useful in electrophoretic applications that require a less-sieving or a non-sieving matrix. Initially they were recommended for stacking gels in multiphasic zone electrophoresis (reference 9), because a stacking gel should impart as little sieving as possible. The opaque polyacrylamide-Bis gels have significant drawbacks. They are brittle, which makes handling difficult. In addition, they are hydrophobic, due to a large proportion of Bis which is more hydrophobic than acrylamide, so that the gels exude water (reference 10). Opaque gels can also be formed, at elevated Bis ratios, even with very hydrophilic monomers such as NAT, or sugar alcohol derived monomers. Many monomer and cross-linker combinations were disclosed in U.S. Pat. No. 5,319,046 and in U.S. Pat. No. 5,185,466. Highly opaque gels were obtained in a number of the combinations. In general, opaque gels have a disadvantage when used as a matrix for electrophoresis, because the detection of separated zones is more difficult due to a high background opacity. Fully transparent gels are therefore preferred, but a certain degree of gel opacity can be tolerated in practice, as evidenced by the widespread acceptance of agarose gels.

There are currently several models which describe the mechanism of gel electrophoresis. According to the extended Ogston model, the electrophoretic mobility of a macromolecule is proportional to the volume fraction of the pores of the gel that the macromolecule can enter (references 11 and 12). The measured electrophoretic mobility, $\mu$, can be related to the free mobility in solution, $\mu_0$, of a migrating molecule with radius R, as well as to the gel percentage T, total length of the gel fibers, l', and the fiber radius, r:

$$\log \mu = \log \mu_0 - \pi l'(r+R)^2 T \quad (1)$$

or $$\log \mu = \log \mu_0 - K_r T \quad (2)$$

where the retardation coefficient, $K_r$, is defined as $$K_r = \pi l'(r+R)^2 \quad (3)$$

The retardation coefficients for various types of macromolecules have been determined by running them in polyacrylamide gels of different percentages. Thus, the $K_r$ values for native proteins of molecular weight of up to 670,000 varied from about 0.04 to 0.20 (FIG. 2, reference 11). Knowing the retardation coefficients, it is possible to calculate relative changes of electrophoretic mobility of proteins after altering the gel concentration. For example, by increasing the gel concentration by 10%, for instance from T=10% to T=11%, the mobility of the smallest protein with $K_r$=0.04 will change by 8.8%. For this calculation it is not necessary to know actual mobilities, since:

$$\mu = \mu_0 \cdot 10^{-K_r \cdot T} \quad (4)$$

$$\mu = \mu_0 \cdot 10^{-0.04 \cdot 10} = \mu_0 \cdot 0.398,$$

and at T=11%

$$\mu = \mu_0 \cdot 10^{-0.04 \cdot 11} = \mu_0 \cdot 0.363,$$

so that at T=11% the mobility is lower by:

$$(0.398 - 0.363) \cdot 100/0.398 = 8.8\%.$$

The largest protein, with $K_r$ of 0.2, would migrate with 36.9% lower mobility after increasing the gel concentration from 10% to 11%. It should be noted that altering the gel concentration by 10% at lower T values would result in smaller changes of mobilities, whereas the changes would be larger at higher T values. In the practice of gel electrophoresis, low gel concentrations are used for the analysis of large macromolecules because at high concentrations they hardly migrate, making the time of analysis unacceptable long.

The retardation coefficients of SDS-protein complexes varied from 0.06 to 0.16 in polyacrylamide gels (reference 13). An increase of the gel concentration by 10%, from 10% to 11%, would result in a decrease of the mobility of the smallest protein by 12.8%, and of the largest protein by 30.8%.

The $K_r$ values have also been determined for double stranded DNA fragments in polyacrylamide gels (reference 14). Over a 100-fold size range, from about 40 to 4,000 bp, the retardation coefficients varied from 0.16 to 0.36. A change in gel concentration by 10%, from 10% to 11%, would cause a reduction in mobility of the smallest DNA fragment by 30.8%, and of the largest fragment by 56.3%. One should note that kilo-base DNA fragments hardly migrate in standard 10% or 11% polyacrylamide gels. Gels of lower percentages have to be used for the analysis of such fragments, and at lower T values the relative change in mobility would be smaller than at 10–11% taken here. From the above calculations related to different types of macromolecules, it is apparent that one can expect at most a 2-fold change in migration rates after altering the gel concentration by 10% in the most commonly used range of gel concentrations.

Another model of gel electrophoresis, called the door-corridor (DC) model, was proposed recently (references 15–19). According to this model, during electrophoresis, macromolecules do not migrate through existing gel pores, but instead they push away gel polymers as they migrate. The gels must contain polymers that can be transiently displaced by the migrating molecules. The macromolecules move in discrete steps and in each step they pass through one gel layer. The essential feature of the DC model is the notion that there are two ways a macromolecule can pass through a gel layer, via a door or via a corridor. Doors are openings formed in the region of a gel layer in which the polymer chains have high motional freedom. Formation of a door does not affect the polymers of other gel layers. Corridors are openings formed in the gel layer where the polymers have low motional freedom. To form a corridor, the migrating molecule must deform a gel layer until an opening develops at a place where one or more polymers end or where the polymers are less cross-linked or entangled. The deformation of one gel layer is accompanied by dislocation of some polymers in at least one layer above and below. If, on the next layer, the migrating macromolecule encounters a similar area, it will again open a corridor. The two corridors may fuse into a single long corridor, spanning several gel layers. To open large corridors, the migrating molecule must be able to sufficiently displace the polymers of different gel layers. The alternative between opening predominantly doors or corridors by a particular migrating macromolecule depends on the balance of two forces. The first force is electrokinetic, and it is exercised on gel layers by all macro-ions moving in the electric field. This force is countered by the resisting force of the polymers in the gel layer, so that the relationship between DNA mobility and the two forces is:

$$\mu = \mu_1 \cdot e^{-F_r/F_e} \tag{5}$$

where $\mu_1$ is the mobility of unit size of the migrating molecule, $F_r$ is the resisting force of the gel polymers and $F_e$ is the electrokinetic force which the molecules use to create openings. In the DC model, the mobility of a macromolecule is thus proportional to mobility of the smallest segment of that molecule, $\mu_1$ which is equal to one base pair for double stranded DNA.

The force with which gel polymers resist migration of a macromolecule will generally increase at higher total gel concentrations, so that mobility of the molecule will be lower. This is in accordance with many experimental findings. The resisting force may be different, however, in two gels containing the same polymers at the same concentration, if the arrangement of these polymers is different. For instance, mobilities of DNA fragments varied greatly in agarose gels cross-linked at different temperatures, even though the gels contained the same amount of polymers (U.S. Pat. No. 5,371,208). In another case, including poly(NAT) gels of equal T and C, DNA migration rates in the gel which included a linear polymeric cross-linker were different from those in the gel which included the branched cross-linker made from the linear one (reference 15). Not only were the mobilities lower in the second gel, but the resolution was also lost (reference 15). The loss of resolution was interpreted as the inability of the migrating DNA molecules to sufficiently dislocate the gel fibers. The results indicated that electrophoretic separation of DNA fragments is possible only in those gels whose polymers can be sufficiently dislocated to allow opening of corridors. Another aspect of the cited finding, related to significantly reduced migration rates in the gels with the branched cross-linker, appeared to be of little practical importance, since the reduced mobilities were accompanied by a loss of resolution. Nevertheless, the results indicated that changes in gel polymers, or in their arrangement, can exert profound influence on the electrophoretic behavior of macromolecules, in accordance with the DC model.

In the prior art it is known that a gel of a particular composition and of a certain total concentration gives optimal resolution of macromolecules only in a limited size range. While there are different definitions regarding which molecule is optimally resolved in a given gel (reference 19), it is general knowledge that outside a certain size range the resolution will be poor. Smaller molecules will give broad bands, whereas larger ones will not migrate sufficiently to be separated in a meaningful running time. Thus, the resolving power in the lower size range is limited by separation efficiency, and in the upper size range by separation selectivity. Separation efficiency relates to the ratio between migration path and zone width, as defined for example in reference 20. A narrow zone width observed after a long migration path, which is equal to sharp bands at the end of the gel, is characteristic for a high separation efficiency. The selectivity is related to the distance between adjacent bands, being better as the distance increases. It is clear that resolving power of a gel can be improved by enhancing the efficiency or selectivity, or both.

The relationship between mobilities of DNA fragments and their size can be illustrated in various ways, of which the most common one is a plot of mobilities versus the log of DNA fragment sizes. The plot of the reciprocal of mobility versus the size of DNA molecules is also frequently used. In the former plot, one always obtains a sigmoidal curve, as shown for example in FIG. 1 of reference 16. From that plot, it is evident that large DNA molecules may all migrate with equal velocity. In some instances a large molecule may migrate faster than a smaller one, causing the phenomenon called "band inversion". While there are different possible explanations for "band inversion" (reference 19), it is clear that this faster migration rate of large DNA molecules limits the possibility of their separation. A lot of efforts have been directed towards understanding and overcoming this limitation. Substantial progress has been made in the ability to separate DNA molecules longer than 20,000 bp by using pulsed electric fields. This improvement relies on the theoretical framework of the reptation model of DNA gel electrophoresis, which is described for example in references 21 and 22. According to this model, DNA molecules orient themselves in the direction of electric field, and the degree of orientation depends on the DNA size and on the applied electric field strength. Once oriented, the molecules reptate through the gel. Their mobilities become independent of sizes, and the resolution is lost. While most of the work aiming to improve DNA separation based on the reptation model was carried out with DNA fragments larger than 1000 bp, there were also reports where the model was used with the goal of improving the separation of smaller DNA molecules. For example, pulsed electric fields were used to improve DNA separation in sequencing gels (reference 23). In addition, the possibility of preventing DNA molecules from assuming the reptating mode of migration by linking a ball-like molecule to one DNA end was studied both in practice and in theory (references 24 and 25).

According to the reptation model, the major role of gel fibers is to prevent sideways motion of DNA molecules, thus keeping the DNA oriented in the direction of electric field. When the gel fibers are spaced further apart, the degree of DNA orientation is lower, and the separation is better. The reptation model thus predicts that low concentration, large pore gels are always better for the separation of large DNA molecules within a given size range. Based on this prediction, there has been a lot of effort expended towards finding novel gels of higher porosity. The most recent work appears to be related to low concentration (3–4%) polyacrylamide gels cross-linked with agarose derivatized with allylglycidylether (reference 26). If orientation of the DNA molecules in electric field represents the major basis for the loss of resolution in the larger size range, then no improvements can be expected by increasing the gel concentration, or by making changes in gel polymers that reduce DNA mobility (effective porosity).

The DC model of gel electrophoresis offers another explanation for the loss of resolution observed for larger DNA sizes. This model predicts that resolution is lost because large DNA molecules form long corridors spanning several gel layers. That happens when gel polymers cannot give adequate resistance to the migrating molecule. If this explanation is correct, then the type and the arrangement of gel polymers play a decisive role, and finding a way to increase the gel resistance should improve resolving power of the gel. The predictions of the reptation model are thus opposite to those of the DC model. Gel resistance was increased in the poly(NAT) gels containing the branched macromolecular cross linker mentioned above, since the migration rates were reduced. However, the reduced migration rates were accompanied by a loss of resolution, presumably because migrating DNA molecules could not sufficiently displace the gel polymers. Thus, a sufficient dislocation of polymers appears to be a necessary condition for a successful separation of DNA molecules by gel electrophoresis.

A further study was undertaken with the aim of developing gels that will give a higher resistance to the migrating DNA molecules, and hopefully prevent the formation of long corridors in gel layers. The desired gels should have a topology which allows polymer dislocation only after application of a larger force, or only after the force is applied for a longer time period. Whether or not such gels could be made was uncertain, because the initial results mentioned above clearly showed that linking the gel polymers in a more stable way can lead to a loss of gel resolving power. New cross-linkers based on polymers other than agarose were screened. Polymeric cross linkers with varying numbers of vinyl groups were prepared, reasoning that a cross-linker may be found with such a number of vinyl groups that will be sufficient to increase the gel resistance without causing the loss of resolution. In one set of experiments, hydroxyethyl cellulose (HEC) was used as the starting polymer into which polymerizable double bonds were introduced by reacting it with allylglycidylether. Poly(NAT) gels containing such a cross-linker were prepared and run. As a control, gels were prepared with HEC which was not subjected to any derivatization. Some of the control gels turned rather opaque after polymerization. Following electrophoresis of DNA fragments in one such gel, two unexpected findings were observed. First, migration rates were lower than in the corresponding gel without HEC. Based on the prior art cited above, higher migration rates were expected for a gel of increased opacity. Second, the migration rates of larger DNA fragments were reduced proportionally more than those of smaller fragments, leading to an enhanced separation selectivity. Once these unexpected results were recognized, it was reasonable to screen other polymers, natural and synthetic ones, in order to get an understanding of the observed phenomenon and to see whether the new gels could be of practical use. As will be disclosed herein under, only some of the polymers were able to generate the same effect, and thus provide gels of enhanced selectivity. Moreover, the enhanced selectivity was achievable only within a certain range of ratios between the cross-linker, the monomer, and the polymer. Outside the critical range, no enhanced selectivity could be obtained even with the best of the three essential gel components, the monomer, the cross-linker, and the polymer.

OBJECTIVES OF THE INVENTION

It is an objective of the current invention to provide electrophoresis gels of enhanced selectivity.

It is another objective of the present invention to provide electrophoresis gels of such an enhanced selectivity that some double stranded DNA fragments differing from 1 to 4 base pairs are separated after migrating less than 10 cm.

It is a further objective of the present invention to provide electrophoresis gels with improved resolving power for DNA molecules in the size range below 1,000 base pairs.

An additional objective is the provision of electrophoresis gels in which sequence-dependent mobilities of double stranded DNA fragments are essentially eliminated.

Another objective of the present invention is the provision of a novel method of gel electrophoresis using as the electrophoresis medium a gel of the present invention.

A further objective is the provision of a method for the preparation of electrophoresis gels of enhanced selectivity.

Other features and advantages of the present invention will become more apparent from an examination of the following specification when read in conjunction with the appended figures.

BRIEF DESCRIPTION OF THE SEVERAL ASPECTS OF THIS INVENTION

In accord with and fulfilling these objects, one aspect of this invention is a novel gel which is suited to use in electrophoretic separation, but which may have other significant uses as well. This gel is the polymeric reaction product of polymerizing a monomeric entity with a cross linker entity in solution and in the presence of a preformed polymer which may be a polymer of the same or of different monomer(s). The monomers and the cross linkers which are used in the formation of the polymeric gel of this invention include those which are commonly known to be useful in forming a gel suited to use in electrophoretic separations. It also includes other monomers which have not yet been identified as being useful in the formation of polymers which are useful in electrophoretic separations. The monomers and the cross linkers may be used as individual compound(s) or as mixtures of suitable compounds. Preferably, the monomers contain vinyl groups and are subjected to free radical polymerization. Suitable conventional free radical initiators may be added to the polymerization solution mixture as needed. The preformed polymer is suitably one or a mixture of materials. It should constitute about 0.005 to 2% (w/v) of the polymerization solution. The mixture of monomer(s) and cross linker(s) should constitute at least about 4% (w/v) of the solution. The solvent is any one or more materials that is a mutual solvent for the monomer(s) polymer(s) and cross linker(s) provided that it does not interfere with the polymerization reaction. Conventional free radical polymerization conditions are used.

In accord with another important aspect of this invention, the gel is most useful as a bed in electrophoretic separations. The electrophoresis is carried out in a conventional manner with the only significant change being the specific nature of the gel bed. In accord with this invention, use of the special gels of this invention enables the electrophoretic separation of mixtures of large and complex molecules such as DNA fragments. The unexpected result which has been achieved by the use of these gels is that the electrophoretic migration of larger molecules is retarded relative to the electrophoretic migration of the smaller molecules. Thus, the components of the mixture of molecules is spread out more in the gel than was possible in the past. In fact, if DNA fragments of a size range of 100 to 3,000 bp are subjected to electrophoresis with the gels of this invention, there is at least a 5 fold decrease in migration of the largest molecules in the mixture as compared to the migration of the smaller molecules in the mixture when the electrophoresis is carried out under identical conditions with the exact same polymer gel except that the preformed polymer is not present during the polymerization reaction.

It is to be understood that the performance of the polymer gels of this invention in electrophoretic separations is not a designation of the use to which these materials are to be put according to this invention. While the use of these gels in electrophoresis is certainly recommended by the findings of this invention, it is by no means a limitation on the scope of the product claims hereof. The results of carrying out electrophoretic resolution of mixed DNA molecules of the recited sizes is however, a very good test to determine if the requirements of this invention have been met.

DETAILED DESCRIPTION OF THE INVENTION

Figure 1:
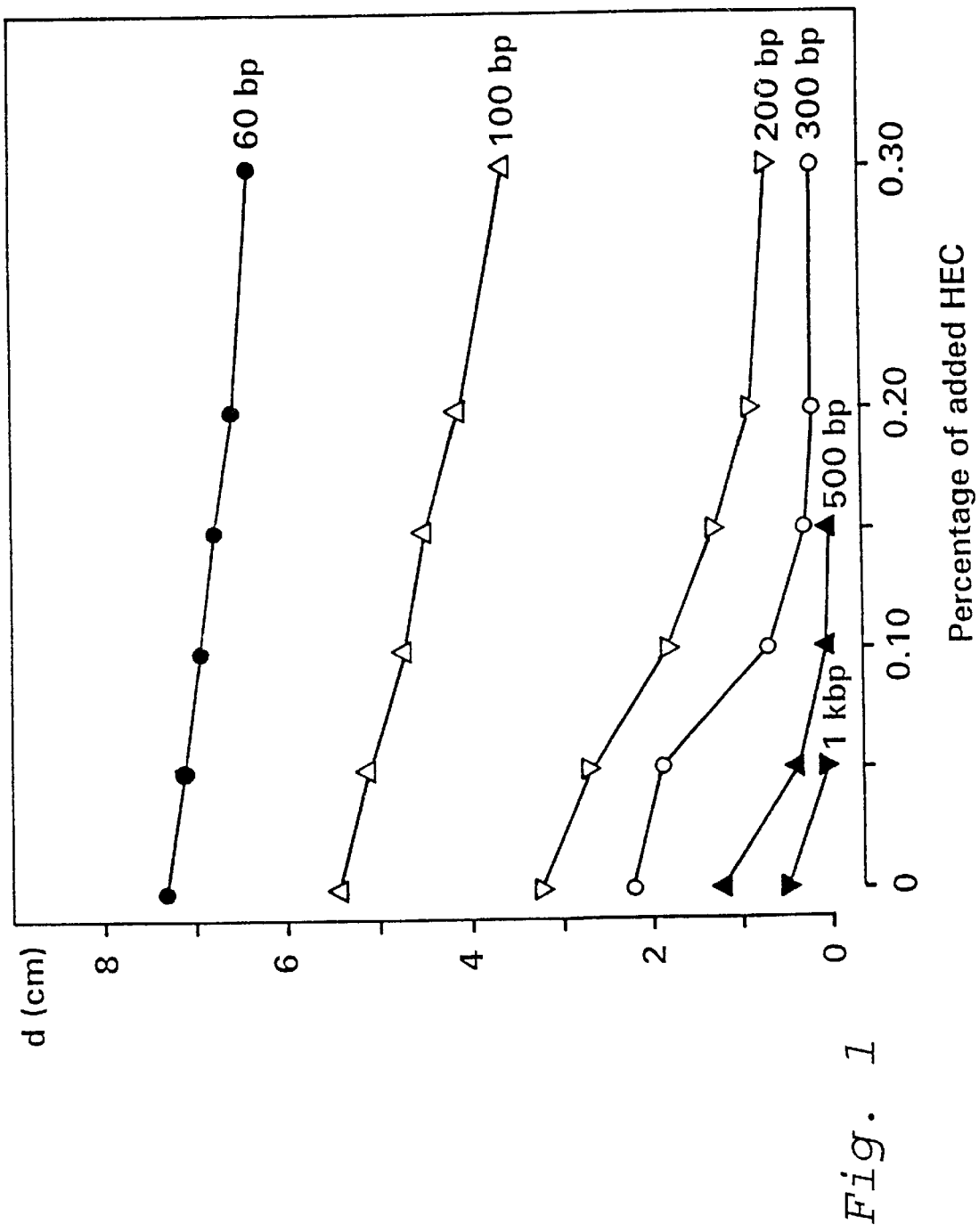
FIG. 1 is the plot of migration distances of 60–1,000 bp DNA fragments versus the percentage of hydroxyethyl cellulose (HEC) added to NAT-Bis solutions of 12% T and 2.6% C. The gels were run at 10 V/cm for 4 h at 20° C., as described in Example 1.

In U.S. Pat. No. 5,371,208, hydroxyethyl cellulose (HEC) was used for the preparation of gels by a cross-linking reaction taking place simultaneously with gelation. The same HEC polymer was added at different concentrations in relation to NAT plus Bis solutions, of 12% T and 2.6% C, prior to their polymerization. As described in Example 1, transparency of the gels with HEC was reduced depending on the amount of the polymer present in the polymerizing solution. Absorbance measurements of 1 cm thick gels, polymerized in cuvettes, were taken at 600 nm. This wavelength was selected since it is at the middle of the visible spectrum. At the lowest HEC concentration, 0.05% (weight per volume), the absorbance was 0.121. At the highest HEC concentration tested, 0.3%, it was 2.239. The control gel without HEC had an absorbance of 0.017. Thus, the presence of HEC polymer during gel polymerization caused a profound change in the gel transparency. Following electrophoresis of DNA fragments of various sizes, a pronounced retardation of larger DNA fragments was observed. The migration distances are given in Example 1, and FIG. 1 shows it graphically. This figure is representative, since a similar pattern was obtained with many other polymers described below. The ratio of migration distances between the 60 bp and 300 bp fragment is 3.32 (7.3/2.2) at zero HEC. At 0.2% HEC, the ratio is more than 10-fold higher, 34.5 (6.9/0.2). In the size range between 100 bp and 200 bp, the ratio has increased 3-fold, from 1.69 to 5.11. It is easy to calculate that in the control gel, with a migration path of 8.7 cm, the 200 bp fragment will migrate 5.1 cm by the time when the 100 bp fragment reaches the end of the gel. In a gel of equal length containing 0.2% HEC, the 200 bp fragment will have migrated only 1.7 cm when the 100 bp fragment comes to the end of the gel. The distance between the two fragments will thus increase from 3.6 cm to 7.0 cm. This enhanced selectivity means that resolving power of the gel has increased by a factor of 2 in the 100–200 bp range.

When poly(NAT) gels of identical T (12%) but varying cross-linking degrees were polymerized in the presence of an equal amount (0.2%) of HEC, the absorbance at 600 nm increased with the cross-linking degree (Example 3). In the gel containing Bis at 1% C it was 0.103, at 1.5% it was 0.321 and at 2.0% it was 0.720. This result indicated that the cross linker molecules are responsible more than the monomer molecules for formation of the species which absorb, or scatter, the light. Additional support for this assumption came from an experiment in which a 12% solution of NAT was polymerized in the presence of 0.2% HEC, but in the absence of Bis. No increase of opacity of the resulting highly viscous solution was observed visually. It should be noted that even though there was a substantial increase of opacity at 1.5% and 2.0% C, selectivity of the gels was improved only slightly. Of the three gels, the largest change in mobility was observed at 2% C with kilo-base DNA molecules, which are anyway poorly resolved in the gels of such a high T value. Therefore, the three gels of 1–2% C offered no advantage in practice.

The implications of the findings obtained by varying the HEC concentration and the cross-linking degree should be considered. An increased absorbance, or scattering, of visible light has been associated in the literature with formation of polymer aggregates, or bundles, whose size corresponds to that of the wavelength of visible light, which is from about 400 nm to 800 nm. Assuming that this interpretation is correct, the above findings then suggest that a larger amount of such aggregates is formed when concentrations of the HEC and the cross-linker are increased. No aggregates are formed without the cross-linker. A question is why the aggregates form in the presence of HEC. Another question is how their structure looks like. The third question is why the gels containing these aggregates show an enhanced selectivity.

Two additional cross-linkers, dihydroxyethylene-bisacrylamide (DHEBA) and piperazine-diacrylamide (PDA), were also co-polymerized with NAT in the presence of HEC (Example 4). The same general pattern was observed, as the absorbance increased at higher cross-linker concentrations, and the gels showed enhanced selectivity. There was one important difference between the cross-linkers, however. Similar absorbance values were reached at various cross-linker concentrations. At 5% C, DHEBA produced a moderately opaque gel, with absorbance of 1.302. With Bis as the cross-linker, at 2.6% C the absorbance was 1.780. With PDA as the cross linker at 1.5%C, the absorbance was 1.998. Since of the three cross-linkers DHEBA is the most hydrophilic one, followed by Bis and PDA, it seems that formation of the aggregates depended on hydrophilicity of the cross-linkers. However, one should not neglect the possibility that the double bonds of the three cross-linkers may polymerize at different rates. Reactivity of the double bonds may have coincided with hydrophilicity of the three cross-linkers. In any case, it is clear that HEC polymers present in the polymerizing solution in all cases caused a change in the arrangement of gel polymers, detectable as a change of the gel opacity.

There are several possibilities as to how the presence of HEC polymers caused the change in gel structure. For instance, cross-linker molecules may have an affinity for the HEC polymers, and thus the local concentration of the cross-linker may be higher in the vicinity of the polymers. Another possibility is that during the polymerization process HEC causes precipitation of the polymers enriched in the cross-linker. The third possibility is that HEC polymers alter the kinetics of the polymerization process in such a way that the cross-linker molecules react preferentially among themselves, rather than with the monomer. Combinations of the three possibilities are also feasible. Regardless of the actual mechanism, the results indicate that formation of the aggregates depends not only on the type of the cross-linker, but also on its concentration. Below a certain concentration, which is different for each cross-linker, the gels with HEC resolved DNA fragments with a power similar to that of the gels without HEC.

HEC polymers of different molecular weight were added to polymerizing solutions containing NAT and Bis. As described in Example 7, all HEC polymers were able to bring about an increase of gel opacity. However, there was a major difference in the ability of the polymers to enhance gel selectivity. The shortest HEC polymers, having molecular weight of 24,000 to 27,000, caused only a minor improvement in the gel resolving power. HEC polymers purchased from Fluka, whose molecular weight was not specified by the producer, were able to bring about a significant improvement. The same was true for the HEC polymers of higher molecular weights, 90,000–105,000, and 160,000 (purchased from Polysciences). These results indicate that formation of the aggregates is not a sufficient condition for the achievement of an enhanced selectivity. The aggregates formed in gels with the HEC of 24,000–27,000 molecular weight behaved differently from those formed in the presence of longer HEC polymers. A difference may exist in the composition of the gel polymers in the bundles, or in the way they are intertwined. It seems more likely, however, that the bundles formed in the presence of one specific polymer have similar composition and structure. If so, then the profound difference in the selectivity indicates that short HEC polymers are not able to bridge, and keep together, the aggregates during passage of the migrating DNA molecules. The polymers need to have a certain minimum length to do so. This conclusion is in accordance with the finding that much lower concentrations of longer HEC polymers were sufficient for achieving a strong enhancement of the selectivity, as disclosed in Example 7.

HEC is an industrial polymer prepared by the action of ethylene oxide on cellulose. The reaction is carried out under rather drastic conditions, and one can expect that side reactions take place. Such side reactions may introduce other functional groups in the polymer. For example, an elimination reaction could introduce double bonds into HEC polymers. The double bonds could copolymerize with NAT and Bis, so that HEC would be covalently linked to the gel matrix. Moreover, HEC produced by different manufacturers, or from different batches and polymer sizes, might have various amounts of substituents. One can imagine that the differences observed were not actually related to various molecular weights, but rather to some other property of the polymers. To resolve this issue, a HEC preparation was subjected to gel filtration an Sepharose CL 6B, as specified in Example 17. Three gels were polymerized with fractionated HEC. The one with the long polymers eluting first, the second with a fraction from the middle, and the third with HEC polymers eluting at the end. Only the gel containing the longest polymers showed a profound enhancement of selectivity, whereas the gel with the shortest polymers showed no change compared to the control gel. Since both polymer fractions originated from the same HEC sample, chemical structure of the polymers should be identical. Accordingly, this experiment firmly established that molecular weight of the polymer has a profound influence on gel properties.

Another aspect of the gel filtration experiment is worth mentioning. The HEC eluted as a very broad peak, indicating that polymer size distribution in this HEC preparation was very broad. The same is probably true for other HEC preparations. Moreover, it was reported recently that the 90,000–105,000 HEC from Polysciences contains polymers of much higher molecular weight (reference 27). Therefore, the molecular weight values given by the manufacturers, and taken as such herein, should be taken with reservation. Polydispersity can be reduced by gel filtration or another fractionation method, if desired. Such more homogenous polymer preparations are also suitable for the preparation of gels of enhanced selectivity, as shown in Example 17.

Gels of enhanced selectivity can also be prepared with other monomers in place of NAT, as described in Example 5. When acrylamide is used as the monomer, Bis as the cross-linker, and HEC as the preformed polymer, a higher cross-linking degree was necessary than with NAT as the monomer. The enhanced selectivity could also be achieved with N-acryloyl-1-amino-1-deoxy-D-galactitol as the monomer (Example 5). These findings demonstrate that the selective retardation of larger DNA molecules in the new gels is not related to any specific monomer. It is not related to any specific cross-linker either, since the gels cross-linked with DHEBA and PDA also showed enhanced selectivity, as described above. While the observed phenomenon thus appears general, it is important to realize that there is only a limited range of concentrations of the monomer and the cross-linker at which alterations of the gel topology will bring about the desired enhancement of selectivity. When this condition is satisfied, many different monomers and cross-linkers are suitable. It is also possible to dissolve more than one monomer and more than one cross-linker in a polymerization solution, as described in Example 6. Such composite gels showed enhanced selectivity as well.

The HEC which was initially employed in combination with NAT and Bis often produced gels of a high background after staining with DNA specific stains. Since the background was more pronounced at higher HEC concentrations, it was reasoned that endogenous DNA present in cellulose could be the cause. The background was indeed lower in gels with HEC which was purified by ion-exchange chromatography over DEAE-Sepharose, as specified in Example 2. However, the gels lost their resolving power. The same thing happened with HEC purified over DEAE Cellulose (Serva). Since the resolving power was restored when the HEC purified over DEAE-Sepharose was passed over CM-Sepharose, it seems that certain positively charged agarose polymers were released from DEAE-Sepharose.

Their amount is expected to be rather low, because crosslinked Sepharose beads were used. The sensitivity of gel resolving power to the presence of small amounts of polycations can be utilized as an analytical method for checking for leakage from commercial cationic ion exchangers. It is likely that a small amount of negatively charged agarose polymers leaked from CM-Sepharose. They are not expected to affect DNA separation, because DNA molecules are also polyanions. A small amount of negative charges is known to exist in the agarose gels used for electrophoresis, without any adverse effects. The method of purification described in Example 2 is suitable for the purification of other polymers prior to their use in the gels for electrophoresis.

Other derivatives of cellulose are also suitable for the preparation of gels of enhanced selectivity (Example 8). Methyl cellulose and hydroxypropylmethyl cellulose, in combination with NAT and Bis, gave gels that showed enhanced retardation of large DNA fragments. These results indicate that the type of the group present in the cellulose polymer is of little importance, even though different groups linked to cellulose are known to influence some of its properties, including solubility, viscosity and hydrophobicity.

Given the described capability of various cellulose derivatives, it was reasonable to test other polysaccharides. Agarose was also able to change the properties of NAT-Bis gels in such a way that the gels showed an enhanced selectivity. The same was true for derivatized agaroses, as disclosed in Example 10. There were some important differences between various types of agarose. For example, much lower concentrations of SeaPlaque agarose than NuSieve agarose were necessary for achieving the same retardation effect. Moreover, the selective retardation was almost completely lost in NuSieve agarose-containing gels that were run at elevated temperature, whereas under the same running condition the gels with SeaPlaque agarose retained their enhanced selectivity. Both, NuSieve agarose and SeaPlaque agarose, are agarose derivatives which contain hydroxyethyl groups (U.S. Pat. Nos. 3,956,273 and 4,319,975), but polymer length in NuSieve agarose is lower. Thus, molecular weight of the agarose polymer played an important role, as was already found for the HEC polymers. Agarose and cellulose are similar in that they are both linear polymers. They differ in their sugar constituents, in glycosidic linkages, and in the ability to form gels. While derivatized celluloses remain in solution at high and low temperatures, agarose polymers form thermally reversible gels. Since the state of association of agarose polymers is temperature dependent, it could be expected that gels of varying selectivity could be produced by changing the temperature of polymerization. That was indeed observed with poly(NAT)-Bis gels containing equal amounts of SeaPlaque agarose but polymerized at different temperatures. The best results were obtained with the gels polymerized at about 35° C., which is above the gelling temperature of this agarose. Very often disturbances were observed in the gels containing various agarose derivatives. The disturbances appeared mostly in the form of wavy, or split, bands. Their origin is probably related to temperature variations across the length, or thickness, of the gel during polymerization. Free radical polymerization is an exothermic reaction, and local temperature variations may influence the state of association of agarose polymers, which in turn could affect the topology of the gel polymers. Nevertheless, one of the best gels with enhanced selectivity was 12% T, 2.6% C gel with 0.2% SeaPlaque agarose. While the polymerization conditions need to be controlled more precisely when a gelling polysaccharide is used, altering of the gel properties by selecting various polymerization temperatures represents an additional option for tailoring the gels of enhanced selectivity.

Other polysaccharides were also used, as described in Example 11. They include dextran, the polysaccharide from locust bean, and carubin-type galactomannan. The locust bean polysaccharide is also a galactomannan, and it was used without further purification after extracting it from locust bean gum. All three are branched polysaccharides. Dextran had a molecular weight of 500,000, whereas the molecular weight of the galactomannan from locust bean was 300,000, as specified by respective manufacturers. While dextran is a highly branched glucose polymer, the galactomannans contain two different monosaccharides, galactose and mannose. The galactose residues occur as branches on a polymannose backbone. All polymers were able to give gels of enhanced selectivity. However, the required concentration of dextran was much higher than that of the galactomannans. With the latter, there was a strong retardation in the gels which contained only 0.01% (carubin galactomannan) or 0.02% (locust bean galactomannan) of the polymer (Example 11). It is possible that with some other polymers, gels of enhanced selectivity could be obtained at concentrations lower than 0.01%, or at another T value, or with another monomer or cross-linker. It is interesting that at higher concentrations tested, locust bean galactomannan caused a loss of gel resolving power similar to the one seen with the HEC that had been passed over DEAE-Sepharose. The cause of this loss was not investigated in detail. The important fact is that all polysaccharides tested could provide gels of enhanced selectivity. While many different polysaccharides have been used, as described in the Examples, there are additional ones which can be suitable. They include starch, levan, glucan, mannan, xylan and other polysaccharides. Gels of enhanced selectivity may contain more than one polymer, as illustrated in Example 13.

Synthetic polymers were also added to polymerization solutions. Polyethylene glycol of two molecular weights (4,000 and 8,000) was not able to give gels of enhanced selectivity, even though gel opacity was substantially increased in the gel which contained 2% of PEG 8,000 (Example 14). Polyvinylpyrrolidone of 360,000 molecular weight did not produce a noticeable increase of gel opacity when added to the polymerization solution at concentrations of up to 0.5%. DNA migration distances in the gels with PVP were similar to those in the control gel. When polyvinyl alcohol of 22,000 molecular weight was used as the polymer, gel opacity changed in dependence on the PVA concentration. However, there was no increase of selectivity. Actually, there was a loss of selectivity and the DNA bands were more diffuse in the gels with PVA than in the control gel (Example 14). These results confirm the conclusion that an increase of gel opacity is not a sufficient condition for obtaining a gel of enhanced selectivity. The three synthetic polymers differed in their structure, and also in their average molecular weight. The presence of PVP in the polymerization solution did not result in a new arrangement of the gel polymers detectable by the method used. That has occurred in the presence of PEG and PVA, but the aggregates were of such a structure, or linked in such a way, that no increase of gel selectivity was achieved.

Linear polyacrylamide was also employed as the polymer. The polymer used had a molecular weight of 10,000 (Polysciences). The presence of polyacrylamide in a 12% T, 2.6% C NAT-Bis solution caused a profound change in gel transparency, as described in Example 15. There was also a strong retardation of larger DNA molecules in the gels containing polyacrylamide. This finding was surprising in view of the results obtained with other synthetic polymers. The gels with polyacrylamide also retained their enhanced selectivity when run at elevated temperatures.

Poly(NAT) polymer was tested following the unexpected finding with polyacrylamide. When added to a NAT plus Bis solution prior to its polymerization, it caused a change in the arrangement of gel polymers in such a way that the gels showed an enhanced selectivity. Thus, the preformed polymer of this invention can be composed of the same repeating monomer units as the gel polymers. The polymer must be added, however, at such a ratio to the monomer and the cross-linker that its presence leads to the formation of gels possessing new defined properties. Those skilled in the art will realize that there are many synthetic polymers which can be suitable. In the first place they include other N-hydroxyalkyl acrylamides, such as those described in U.S. Pat. No. 5,185,466. Other N-hydroxyalkyl acrylamides, as well as other vinyl monomers, are known from the literature. The polymer may also contain units derived from more than one monomer. Preparation of such co-polymers is straightforward when the polymerization rate of different monomers is comparable. For preparing the gels of present invention it is required that the polymer be soluble in the same solvent in which the monomer and the cross-linker are dissolved. Water will be the solvent of choice in most cases, but other solvents, or mixtures of solvents, may be used as well.

The magnitude of selective retardation in the new gels is most surprising. It was expected that migrating molecules will be retarded upon increasing the total gel concentration. As noted above, however, after increasing the gel concentration by 10% it was reasonable to expect at most a two-fold decrease of migration rates, based on the extended Ogston model. The reptation model does not allow predictions about changes of electrophoretic mobility with gel concentration. In the new gels, the total gel concentration was increased often by less than 1%, for example in 12% T gels containing 0.1% of a polymer, but migration rates of longer DNA fragments changed frequently by more than one order of magnitude. Actually, over 100-fold lower DNA mobilities were detected in some gels, after 15 h long electrophoresis at 10 V/cm. It is noteworthy that DNA fragments which migrated just a few millimeters after an overnight run showed sharp bands in many gels. Thus, a strong retardation was not associated with a loss of gel resolving power, as was the case earlier with the gels which contained macromolecular, branched cross-linkers (reference 15).

In addition to the three models of gel electrophoresis mentioned above, a fourth one proposes that electrophoretic migration of macromolecules can be described in terms of gel viscosity (references 28 and 29). It was of interest, therefore, to measure viscosity of solutions of various polymers that were added to polymerizing solutions. The measurements were carried out at 20° C., usually at polymer concentrations identical to those existing in the gels, by using a falling ball viscosity meter (Gilmont). The viscosity meter was calibrated with water. The purified HEC (Fluka) solution at 0.2% had a viscosity of 1.5 cps. The purified HEC (90,000–105,000 MW, Polysciences) solution at 0.2% showed a viscosity of 2.9 cps. The viscosity of 0.5% PVP (360,000 MW) was 1.4 cps, of 0.2% solution of galactomannan (carubin type, Senn Chemicals) 4.5 cps, and of 2% PEG 8,000 it was 1.5 cps. Thus, HEC (Fluka), PVP and PEG solutions had a similar viscosity, but the gels containing these polymers had profoundly different selectivity, as disclosed in the respective Examples. Therefore, based on viscosity measurements it is not possible to predict whether a polymer will provide gels of enhanced selectivity. On the other hand, in the group of polymers which caused an improvement of gel selectivity, selective retardation of larger molecules was stronger with polymers of higher viscosity. In the case of HEC that was expected, since viscosity is proportional to polymer size and previous experiments established that longer polymers cause a stronger retardation effect. It is important to note that in general the viscosity of polymerizing solutions with a polymer was at most a few fold higher than the viscosity of the control solution without the polymer. Since mobilities of some DNA molecules were often reduced by more than one order of magnitude, it is not possible to correlate mobilities of DNA molecules and viscosity of the polymerizing solutions.

Figure 2A:
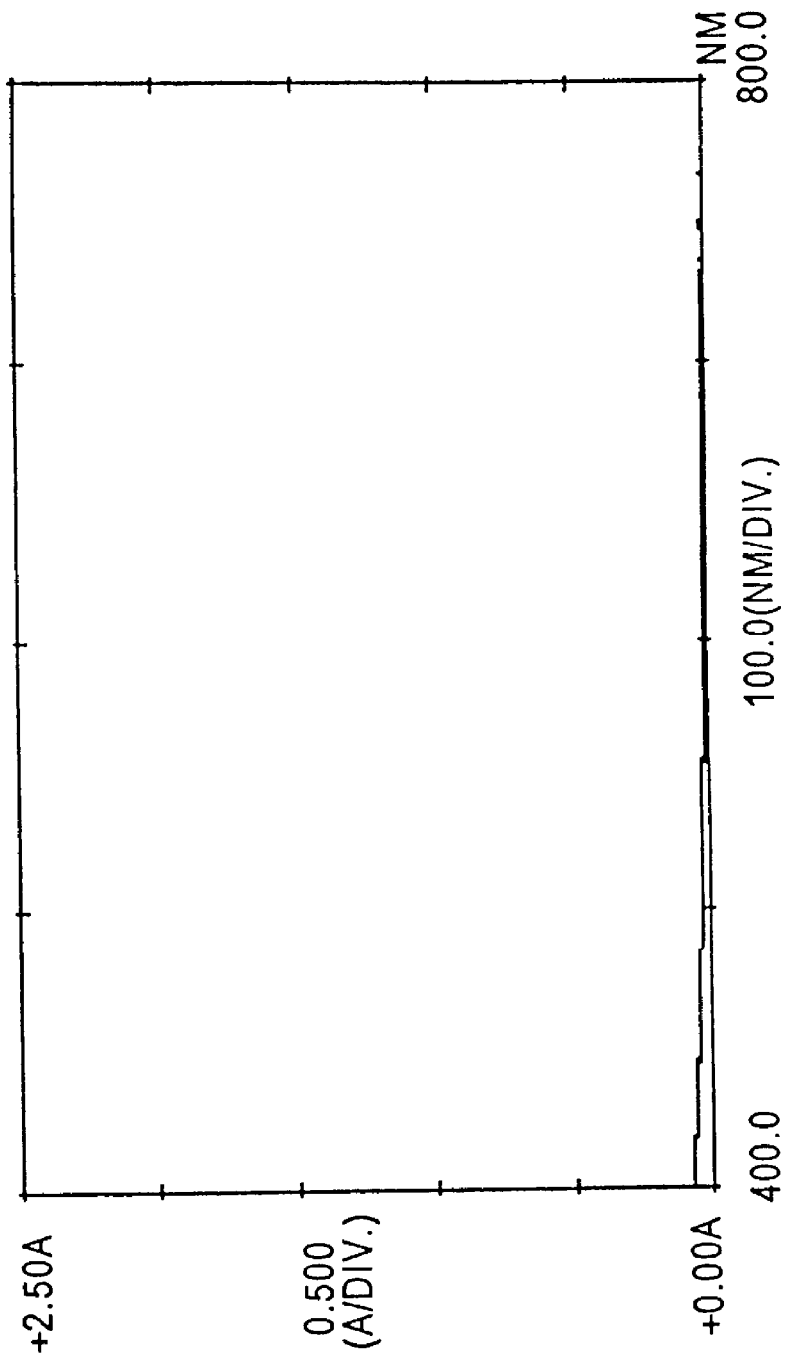
FIG. 2A–F show spectra of the 12% T, 2.6% poly(NAT)-Bis gels containing various percentages (w/v) of added HEC, including 0 (FIG. 2A), 0.05 (FIG. 2B), 0.10 (FIG. 2C), 0.15 (FIG. 2D), 0.20 (FIG. 2E), and 0.3 (FIG. 2F).
Figure 2B:
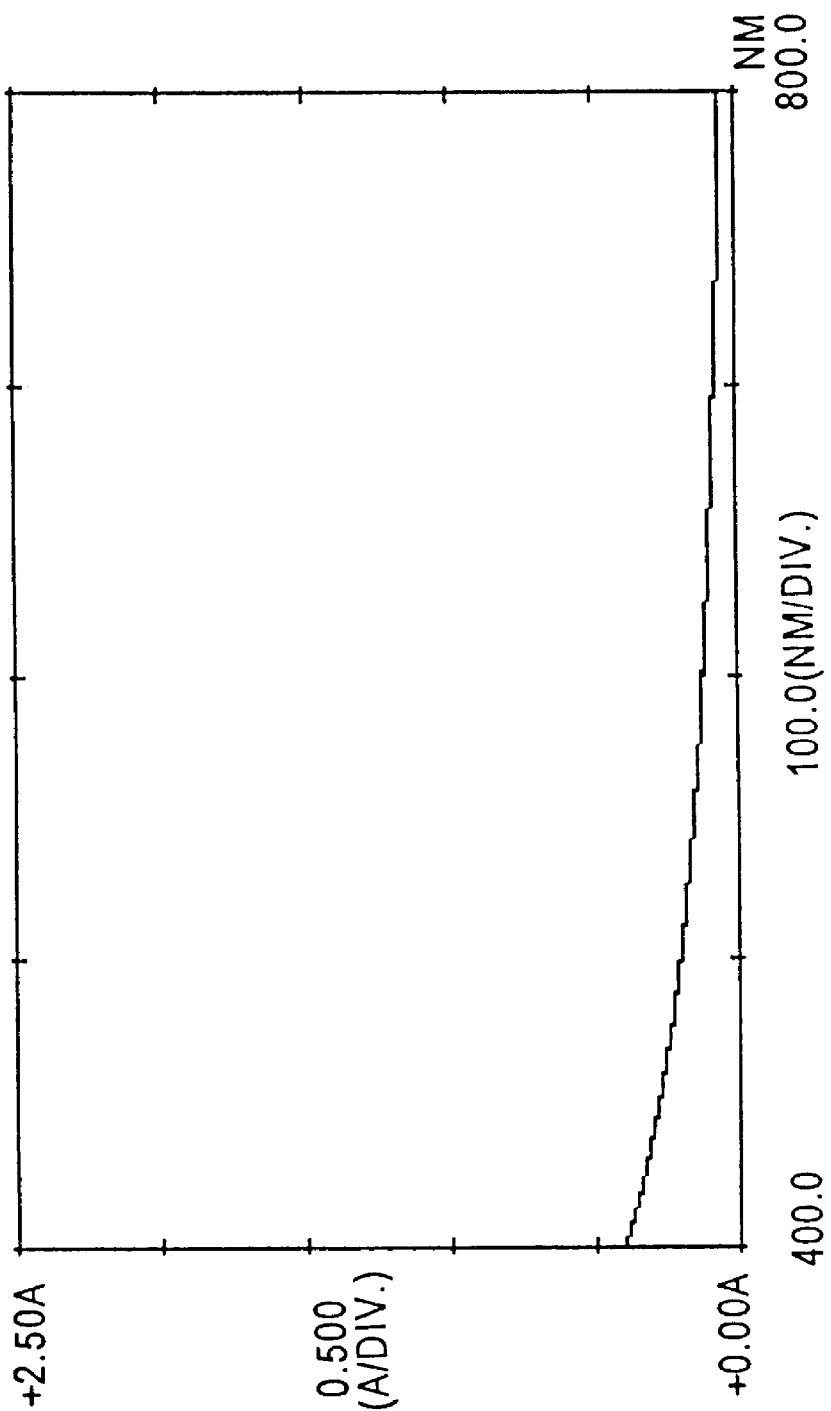
Figure 2C:
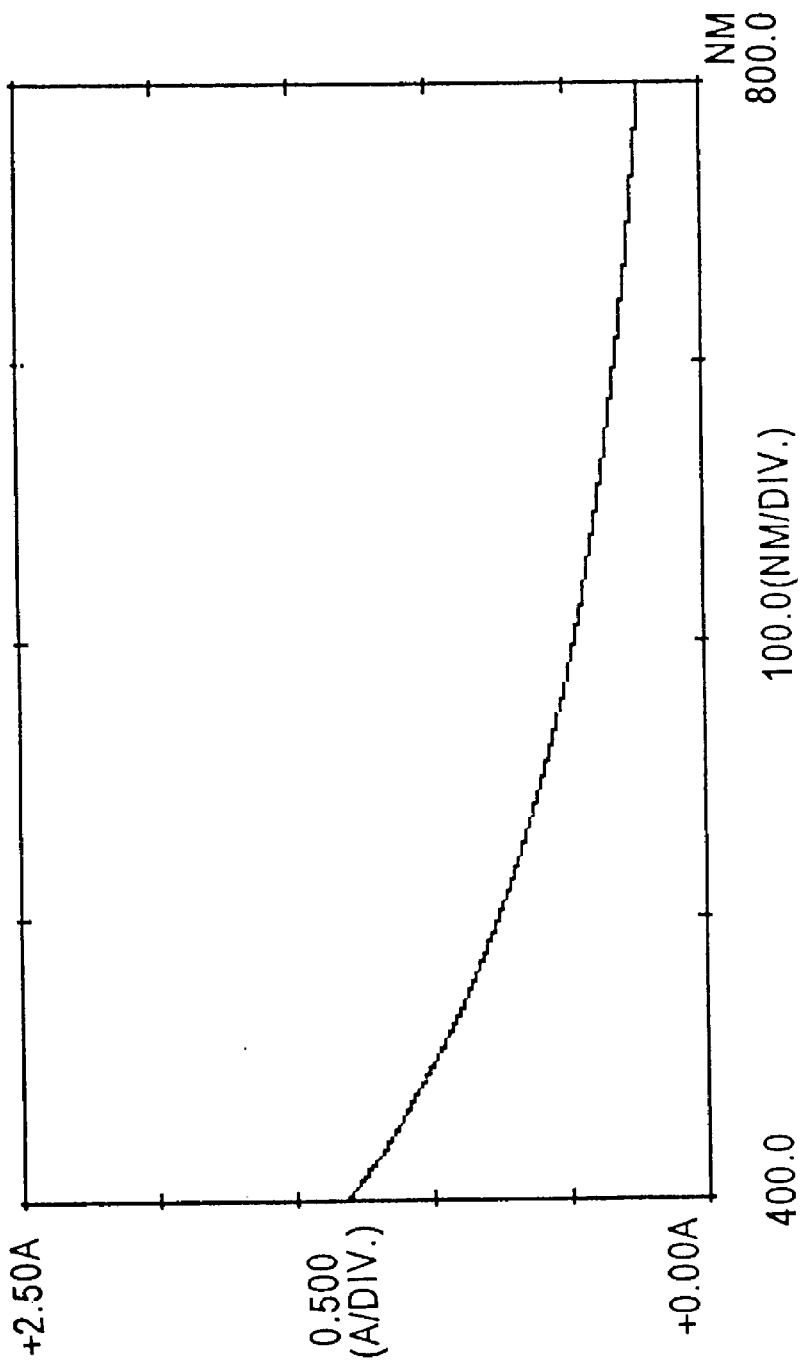
Figure 2D:
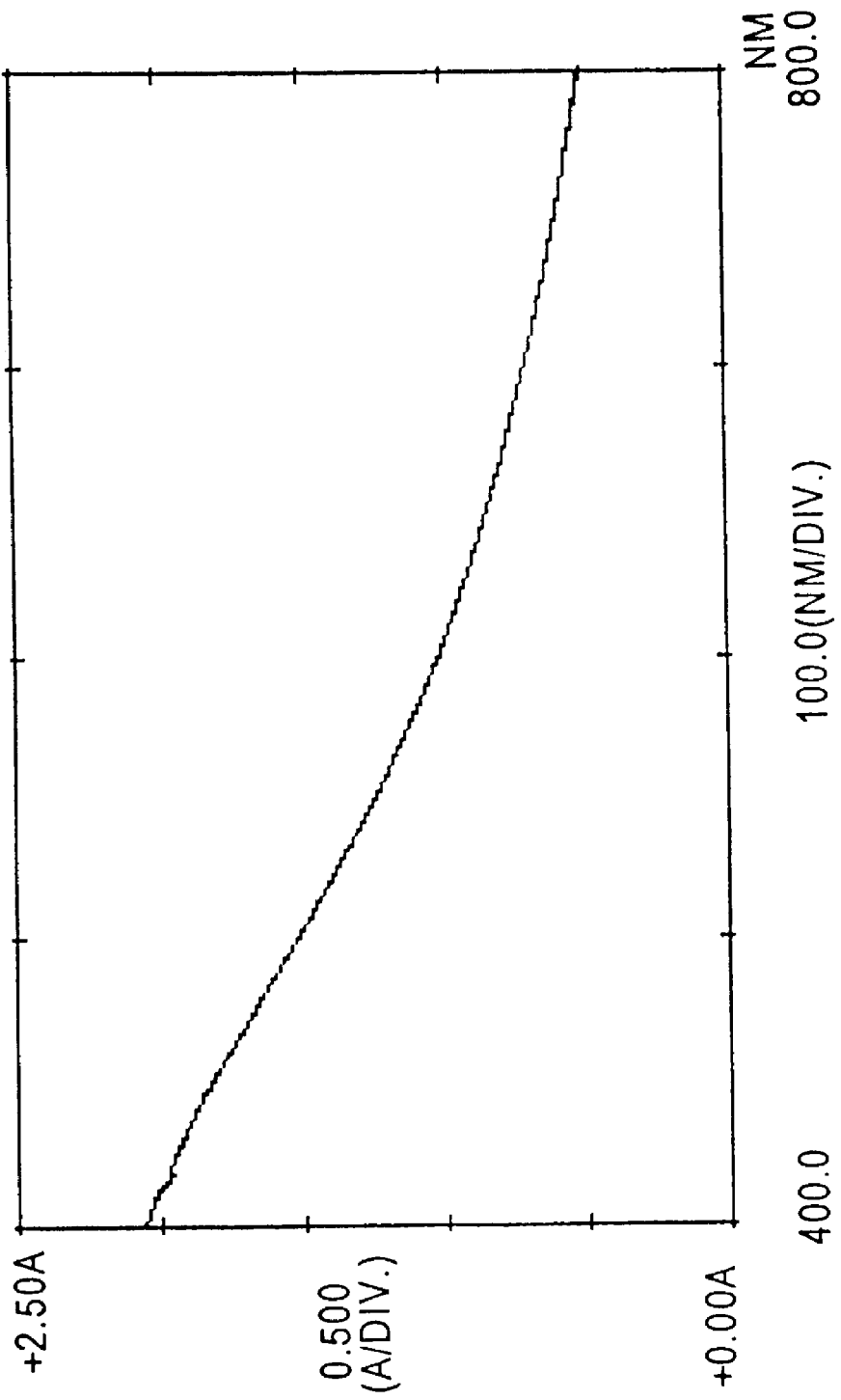
Figure 2E:
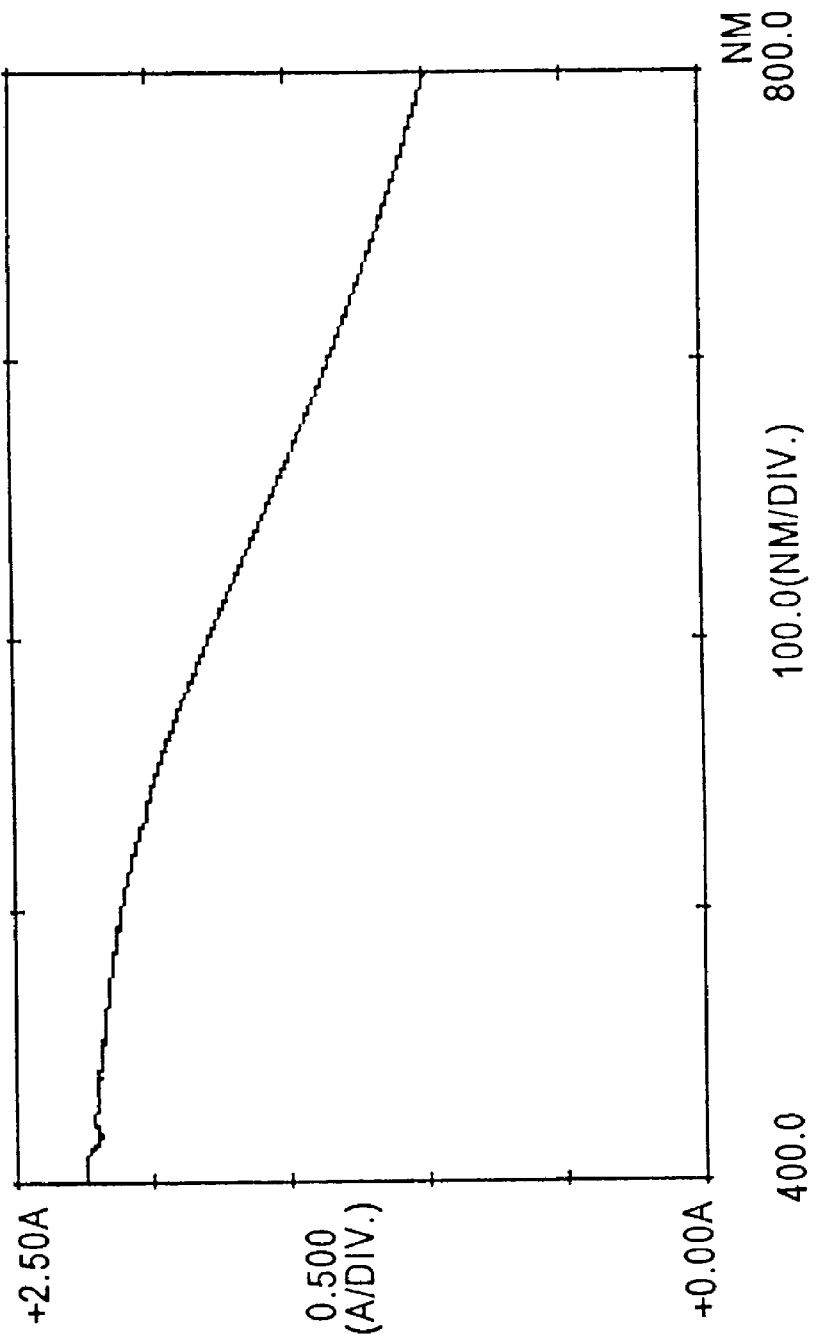
Figure 2F:
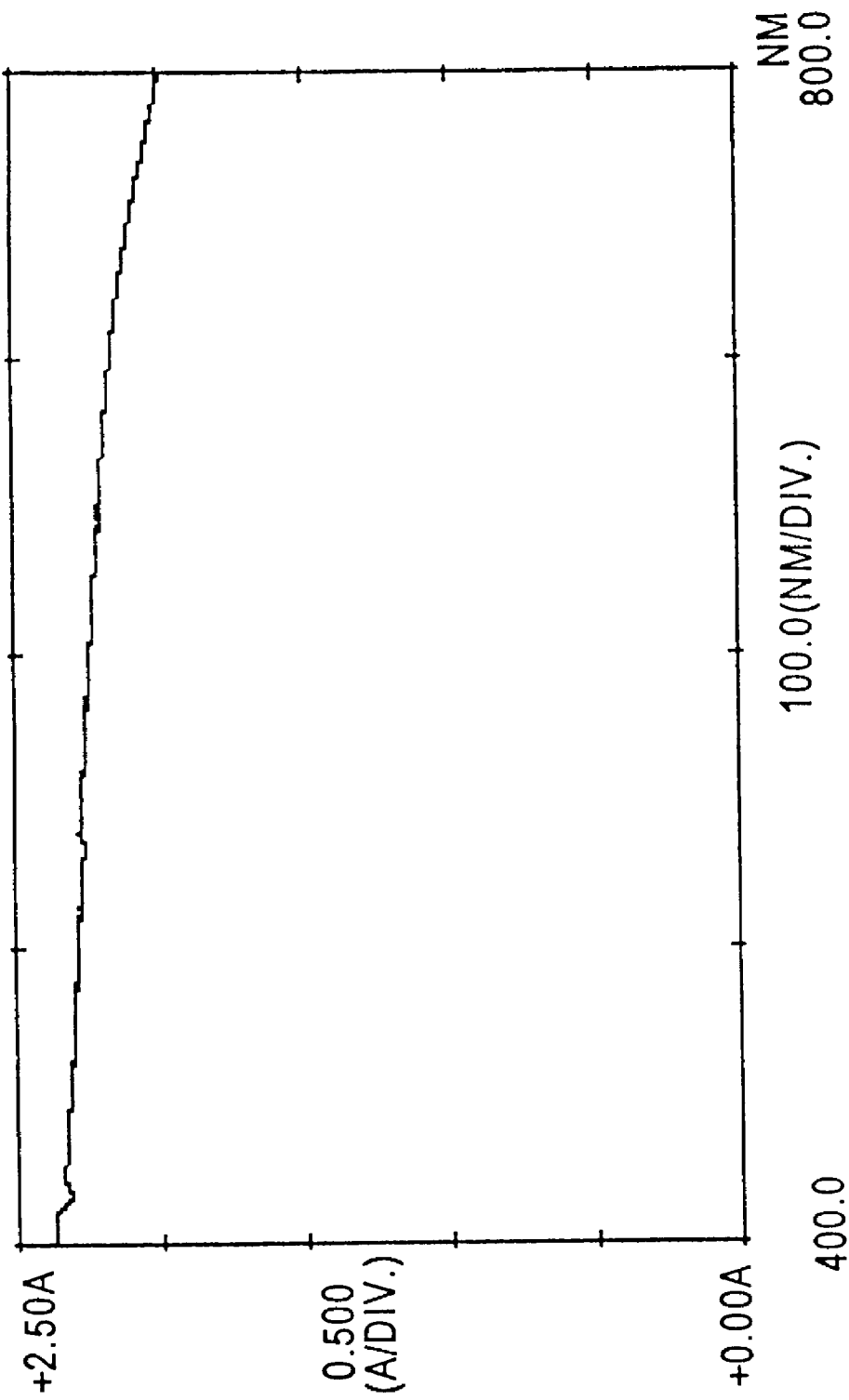

In the practice of the present invention, the polymers present during gel polymerization cause such a change in gel structure that large DNA molecules migrate at reduced rates. The change in gel structure was measured in terms of gel opacity, or transparency. It is noteworthy that while a change in the opacity was always observed in new gels, the magnitude of the change varied greatly, as disclosed in the Examples. From that magnitude it was not possible to say whether a gel will, or will not, have an enhanced selectivity. In some cases, gels with only a minor increase of opacity showed good selectivity, for example those containing 0.02% locust bean gum or 0.01% carubin-type galactomannan (Example 11). The absorbance at 600 nm of these gels was only about 0.08. It is possible that gels with even a smaller change in optical properties, or without any detectable change, will also show improved selectivity. Moreover, another method of detecting changes in the polymer topology could be better suited for correlating these changes to enhanced selectivity. Spectra recorded over a broad wavelength range give more information than absorbance measurements at a single wavelength. Many spectra in the 400–800 nm range were recorded, both of gels polymerized in cuvettes, and of 3 mm thick gel pieces. FIG. 2 shows such spectra of 12% T, 2.6% C poly(NAT)-Bis gels, without HEC (FIG. 2A), or with 0.05% HEC (FIG. 213), with 0.10% HEC (FIG. 2C), with 0.15% HEC (FIG. 2D), with 0.20% HEC (FIG. 2E), and with 0.3% HEC (FIG. 2F). The strong increase of gel opacity with increasing HEC concentrations is evident. Similar spectra were obtained with many other polymers. From the spectra it was not possible to predict which gel will show an enhanced selectivity. Gels with similar spectra containing different polymers often showed profoundly different selectivity. In one case, when PVA was used as the polymer, the increase of absorbance in the 400–800 nm range was associated with worsening of the selectivity (Example 14). While from the spectra it was not possible to foresee whether a gel will possess enhanced selectivity, it was possible to predict which gel will have poor resolving power due to broad bands. In all cases investigated, the DNA bands were invariably broad and diffuse when absorbance of a gel was above 2.0 in the whole 400–800 nm range. Such gels often showed a strong background staining. Moreover, from the spectra in the visible region, it was observed that the ratio of absorbances at 400 nm and 800 nm generally decreased with increasing polymer concentrations. This ratio was the highest with the gels without any added polymer, but the absolute absorbance values were the lowest. For instance, a 12% T, 2.6% C NAT-Bis control gel had the absorbance at 400 and 800 nm of 0.109 and 0.008, respectively, whereas the absorbance values were 0.656 and 0.101 for the gel of equal T and C with 0.02% carubin-type galactomannan. Identical behavior was observed with many other gels. This finding indicates that the amount of larger aggregates increased proportionally more than the amount of smaller aggregates. In absolute terms, however, the amount of smaller aggregates was always higher than the amount of larger ones, judging from the higher absorbance at 400 nm than at 800 nm in all gels.

A change in gel polymer arrangement, detected as an increase of gel opacity, is not sufficient for producing gels of enhanced selectivity, as discussed above. One polymer which caused a pronounced change in gel opacity without improving the selectivity was PEG 8,000. PEG is a linear polymer, composed of small —$CH_2$—$CH_2$—O— repeating units. There will be little friction when such a polymer is pulled through a network of other polymers. Polyvinyl alcohol, with the structure —$CH_2$—CH(OH)—, also contains small repeating units. Opacity of the gels with PVA increased, but not the selectivity (Example 14). These findings indicate that the polymers of present invention need to possess repeating units of a certain minimum size in order to afford enhanced selectivity. Polyacrylamide, —$CH_2$—CH($CONH_2$)—, already satisfies this criterion as it provided gels of enhanced selectivity (Example 5). Polymers with bulky repeating units were generally effective. An exception was polyvinylpyrrolidone, but this polymer did not cause a measurable change in gel opacity in the first place. It is important to note that even if the polymer structure is proper, there will be no enhanced selectivity if the polymer chains are too short. This is illustrated with the inability of HEC of 24,000–27,000 molecular weight to produce gels of sufficiently enhanced selectivity.

A polymer of correct structure and molecular weight is the one whose presence during gel polymerization results in a gel characterized by a strong reduction of migration rates of large DNA molecules. That reduction might be related to a high friction between gel polymers. If DNA molecules displace gel polymers during gel electrophoresis, as proposed by the DC model, then any increase of friction between gel polymers will slow down the movement of DNA. Small DNA fragments need to displace only a few polymers. The large ones push away many, in order to form openings through which they will migrate. When a gel contains polymer aggregates, then large DNA molecules displace these aggregates. If the aggregates are linked together by another polymer, then the migrating DNA may not be able to displace the aggregates due to a high friction inside the aggregates between gel fibers and the preformed polymers linking the aggregates. The new gels are thus able to give adequate resistance to the migrating DNA molecules. Is it realistic that such an increase of friction can be generated? In a recent article (reference 30), the behaviour of polymers confined into a narrow space was discussed. New dynamic behaviour emerges when the available space approaches that of the polymer size. A lot of activities is currently directed towards better understanding of nanorheology, that is deformation of substances confined into a space of molecular dimensions (reference 30). The situation treated in the specified reference is different from the present one, due to the absence of an electric field and the migrating molecules. Nevertheless, it gives support to the view that a huge increase of friction might occur when the space for polymer dislocation is limited. It is proposed here that such a situation exists in gel aggregates. The aggregates formed in the presence of a polymer are probably enriched in the cross-linker, as noted above. Owing to an increased level of cross linking, and due to a high local concentration of the gel polymers, inside the aggregates the added polymers have little free space. In addition, along their length there may be loops and hairpin structures, intertwined with gel polymers. Displacement of two aggregates necessitates that the added polymers are pulled out from one of them. If that requires a higher force than a migrating DNA possesses, then the DNA will not migrate at all. DNA bands that remained at the wall of the sample well were observed in many new gels of this invention, as specified in Examples.

Figure 3:
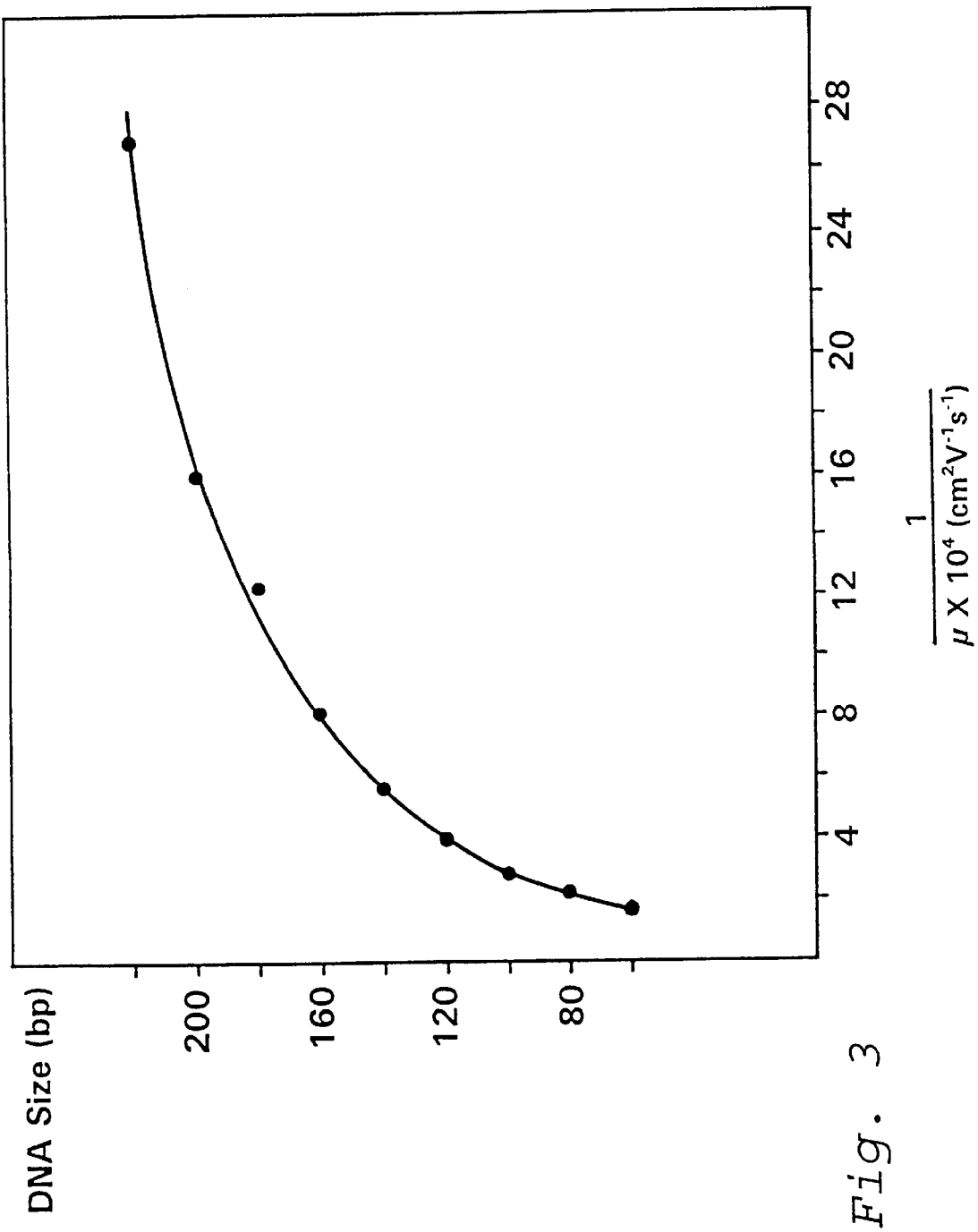
FIG. 3 shows a plot of the DNA fragment sizes versus the reciprocal of their mobilities determined in a 12% T, 2.6% C poly(NAT)-Bis gels containing 0.2% SeaPlaque agarose, run at 10 V/cm for 4 h at 20° C.
Figure 4:
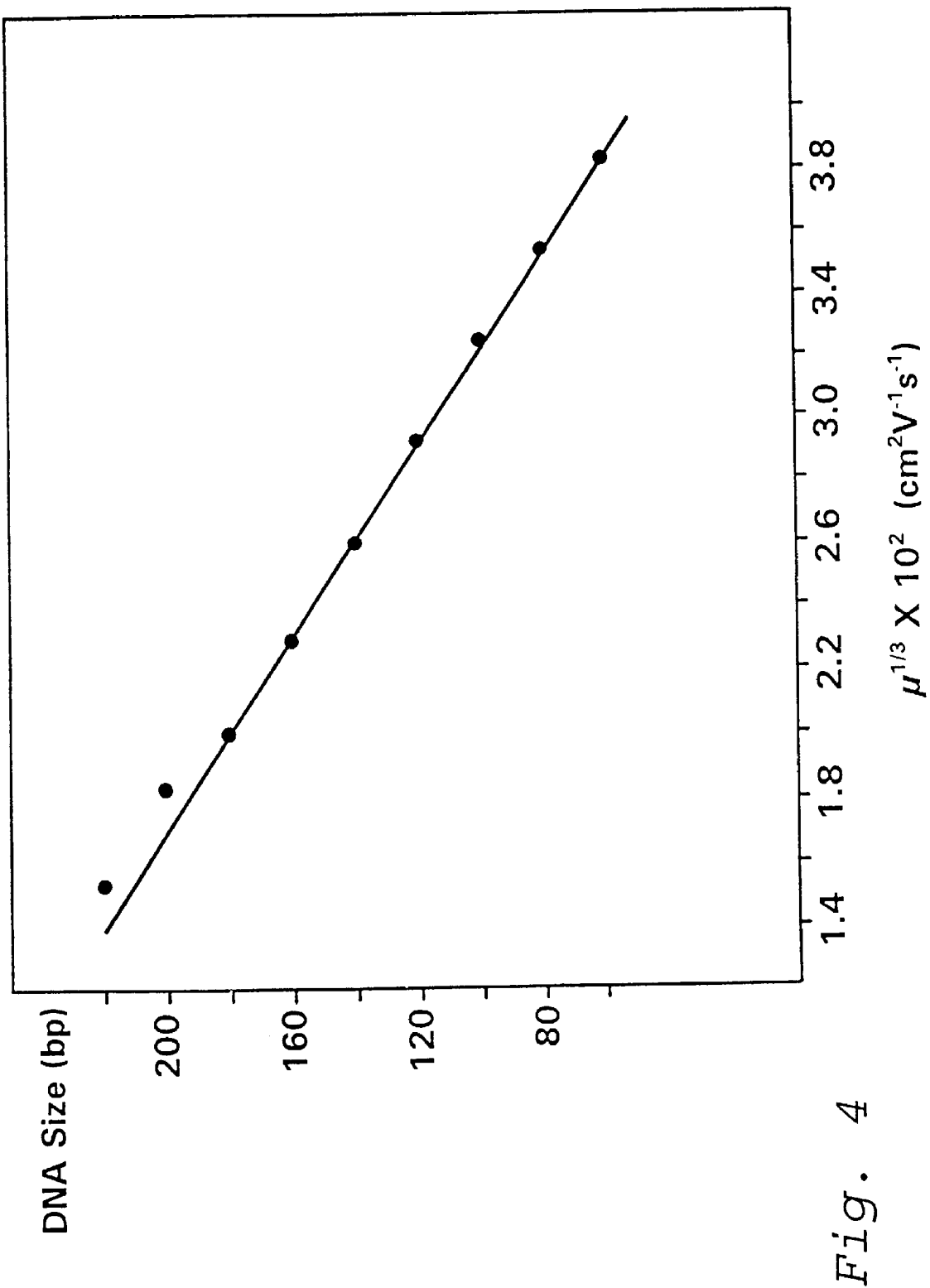
FIG. 4 is a plot of the DNA fragment sizes versus $\mu^{1/3}A$ where the $\mu$ values are identical to those of FIG. 3.
Figure 5:
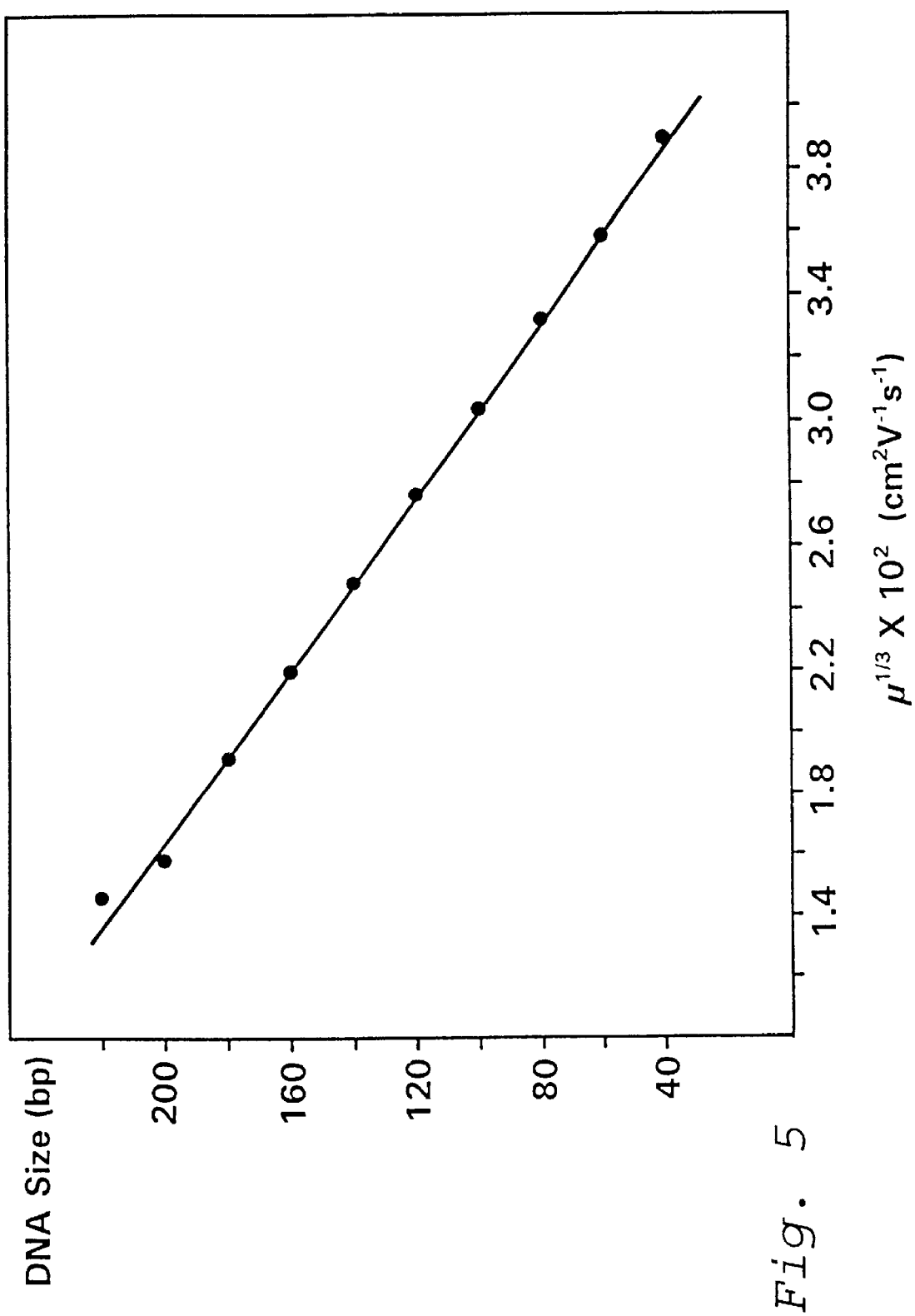
FIG. 5 is another DNA size versus $\mu^{1/3}$ plot, obtained with the mobilities determined in a 12% T, 2.6% C poly(NAT)-Bis gel containing 0.1% (w/v) of linear polyacrylamide (MW 10,000). The gel was run at 10 V/cm for 4 h at 20° C.

If in the new gels there is a higher friction between gel polymers and migrating DNA molecules, that could result in a different relationship between the DNA size and mobility. Indeed, that was noticed after plotting the size of DNA fragments versus the reciprocal of their mobilities. In standard gels of many different chemical compositions, including those composed of natural, semi-synthetic, and synthetic polymers, there is a linear relationship between DNA sizes and the reciprocal of their mobilities, as reported previously (references 16–18). This relationship was studied in detail with only some of the new gels. In a 12%T, 2.6% C gel with 0.2% SeaPlaque agarose, the plot of DNA size versus the reciprocal of mobilities shows a strong curvature (FIG. 3). Much better linearity was observed when the DNA sizes were plotted against $\mu^{1/3}$ in FIG. 4. A straight line was obtained also with a 12% T, 2.6% C gel containing of 0.1% polyacrylamide (10,000 MW), as shown in FIG. 5. Thus, a new relationship between the sizes of DNA fragments and their mobilities exists in the gels of present invention. From the plots shown in FIG. 4 and 5, one can estimate the $\mu_1$ value by extrapolation, and then by using equation 5 calculate the friction between migrating DNA molecules and gels fibers, in the manner described previously (references 16–19). The calculated friction was much higher than in old gels, but the details are beyond the scope of present specification.

Figure 6:
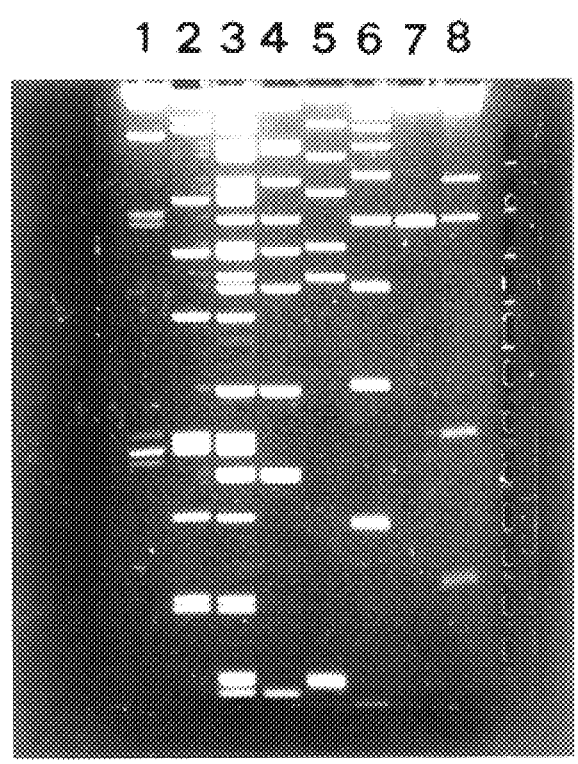
FIG. 6 is a picture of a 12% T, 2.6% C poly(NAT)-Bis gel containing 0.3% (w/v) of poly(NAT), electrophoresed at 10 V/cm for 12 h at 20° C. The following DNA samples were applied to the gel: lane 1, 50 bp ladder (Pharmacia); lane 2, pBR322/HhaI; lane 4, pBR322/MspI; lane 5, pBR322/HaeIII; lane 3, mixture of the three pBR322 digests; lane 6, 20 bp ladder (Gensura); lane 7, 100 bp ladder (Gensura), and lane 8, 1 kb ladder (Life Technologies).
Figure 7:
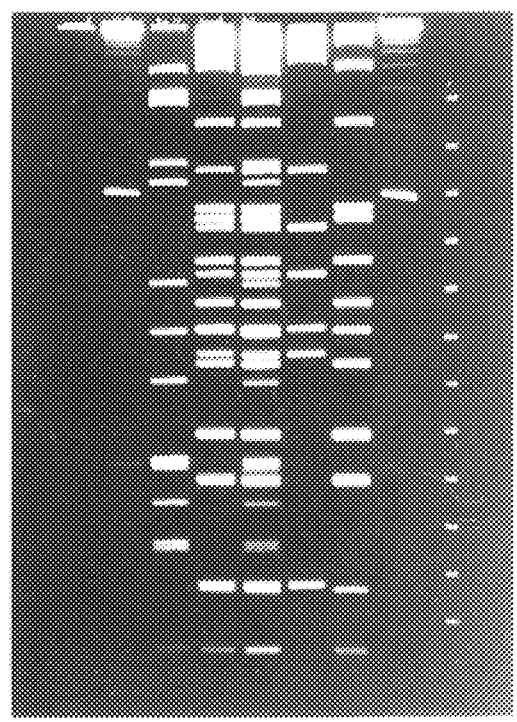
FIG. 7 is a picture of a 12% T, 2.6% C poly(NAT)-Bis gel containing 0.2% (w/v) of SeaPlaque agarose, run at 10 V/cm for 2.5 h at 62° C. The DNA samples are: lane 1, 50 bp ladder (Pharmacia); lane 2, pBR322/HhaI, lane 3, mixture of two pBR322 digests, including pBR322/HaeIII and pBR322/MspI; lane 4, mixture of the three pBR322 digests; lane 5, pBR322/HaeIII; lane 6, pBR322/MspI; and lane 7, 50 bp ladder.

Anomalous, sequence-dependent DNA mobilities are the major limitation of DNA size estimation by gel electrophoresis. It was surprisingly observed that in some of the new gels the anomalous mobilities were largely suppressed even when the gels were run at 20° C. Examples of such gels are poly(NAT)-Bis (12% T, 2.6% C gels containing 0.2% SeaPlaque agarose, and the same gels containing poly (NAT). FIG. 6 shows the gel with 0.3% of added poly(NAT), electrophoresed at 10 V/cm for 12 h at 20° C. Anomalous mobilities are completely eliminated when the gels were electrophoresed at 55°–65° C., as judged from three different pBR322 digests run in adjacent lanes of a 12% T, 2.6% C gel containing 0.2% SeaPlaque agarose (FIG. 7). The gel was run at 10 V/cm for 2.5 h at 62° C. Sizes of the DNA fragments obtained by digestion of pBR322 with various restriction enzymes were taken from Molecular Biology Labfax (T. A. Brown, Ed., Blackwell Scientific Publications, Oxford, UK). There are currently two views regarding the mechanism responsible for anomalous DNA mobilities. One view stipulates that anomalously migrating DNA molecules are curved, whereas the other view assumes that such molecules exhibit increased flexibility at some junctions. While a discussion on which view is supported by present results is out of scope of this invention, it is important to realize that new gels are advantages for those applications that require a precise estimation of DNA fragments sizes.

In new gels, not only are the anomalous mobilities largely eliminated, but the gels are also able to resolve 1 bp differences between DNA fragments in the 100 bp range. Such resolution is shown in FIG. 6, where the fragments of 131 and 132 bp, and also of 151, 152, and 153 bp, are resolved in the pBR322/HhaI digest (lane 2 and 3). Thus, the enhancement of selectivity enabled fine resolution on a much shorter gel length than previously possible. It is noteworthy that 4 bp differences in the 200 bp range were resolved after the DNA fragments migrated only about 2 cm, again demonstrating the enhanced selectivity (FIG. 6, lane 3). It is clear that gel length of the new gels can also be longer than exemplified here. The important fact is that substantially shorter gels are sufficient for achieving the same resolution compared to old longer gels. Short gels are preferable not only because they are easier to cast and handle, but also because they require less reagents for gel preparation and for detecting separated bands. Moreover, bands are sharper in short gels, since band width increases with migration distance.

Gels of the present invention can be run in various formats, which are known in the prior art. As disclosed in the appended Examples, most gels were run in submerged gel electrophoresis mode, but some were run vertically (Example 9). It is possible to run them also in the flat-bed and capillary mode. Each of these modes has advantages for specific applications, and those of ordinary skill in the art are aware of the usual adaptations which need to be done when changing one electrophoresis mode for another. The gels can be run at different electric field strengths. Most present gels were electrophoresed at 10 V/cm in order to allow easy comparison of different gels. Some gels were also run at a lower voltage (Example 8), and also at a higher voltage. At 15 V/cm in the submerged mode, the tested gels with HEC, polyacrylamide and poly(NAT) retained their enhanced selectivity. Higher electric field strengths can be applied when employing thin gels or gel-filled capillaries. The gels can be used at various temperatures, as illustrated by many Examples. While present gels were used here for analytical applications, they can be employed for preparative usages as well. During electrophoresis the migrating molecules may migrate entirely through a new gel, or the new gel may represent only a part of the separation matrix. Gel length can be varied to satisfy the requirements of specific separation needs. Due to the high selectivity of the new gels, very short gels, with a length of 1 mm or less, may provide the required resolution. Gel thickness can be also varied, and ultra thin gels are generally best suited for fast runs. The gels can be made also in the form of membranes. The total gel concentration is varied in accordance with the size range analyzed. The lowest gel concentration is limited by polymerization efficiency of the monomer, and it will be about 4% in most cases. The highest gel concentration is determined again by the size range of the molecules being separated, and also by solubility of the monomer. Gel concentration may vary along its length, and such gradient gels might be beneficial in some applications. It is also possible to make gels with a gradient based on the polymer concentration.

Their enhanced selectivity was retained in the presence of a denaturant, urea, as disclosed in Example 16. Electrophoresis under denaturing conditions is used for DNA sequencing, and this application can also benefit from the enhanced gel selectivity. It is important to note that the ratio of essential gel components may need an adjustment when the polymerization is carried out in the presence of a denaturant, as described in Example 16.

In the gels of present invention, selective retardation was investigated in detail only with DNA molecules. Other macromolecules may behave in a similar way. It was of interest to find out whether large proteins will also be selectively retarded. Electrophoresis was carried out in the vertical format using Bio-Rad Mini Protean electrophoresis unit. When native proteins in the size range from 660,000 Da to 66,000 Da (Pharmacia High Molecular Weight Markers) were run in a 9% T, 2.6% C poly(NAT)-Bis gel containing 0.06% HEC (MW 90,000–105,000), there was hardly any difference in the migration distances compared to the control gel without HEC. Large DNA molecules were strongly retarded in the gel of identical composition. While it is possible that the ratio of the essential gel components was not optimal for protein separation, the above finding may indicate that the mechanism of protein migration through gels is different from the mechanism of DNA migration. That assumption seems to be in agreement with results described in a paper on electrophoresis of SDS-proteins in polyacrylamide gels containing various polymers (reference 31). One should note that native proteins were run here and denatured proteins in the cited publication. Only moderate changes of the selectivity were reported in reference 31. Interestingly, smaller SDS-proteins were retarded proportionally more than the larger ones. That result is just the opposite from the findings described herein, where larger DNA molecules were retarded more than the small ones. In the reference, the cross-linking degree of polyacrylamide-Bis gels was much lower (2.66%) than found optimal in this work for DNA separation. Moreover, opacity of the gels was not measured, so that it is impossible to make comparisons of optical properties. The low cross-linking degree can be the major reason for the difference between the results of this work and those of the cited publication. It is also possible that the mechanism of electrophoretic migration of SDS-protein complexes is different from the mechanism of DNA migration. In that case, the results obtained with SDS-proteins are not relevant for DNA, and vice versa. Further work is necessary to clarify this issue.

The present finding that separation selectivity of polyacrylamide-Bis gels could be substantially improved is surprising in view of extensive study of this matrix over many years. Upon completion of the experimental work described herein, additional examination of the literature revealed two interesting papers. In the first one (reference 32), the authors studied the possibility of determining free mobility by using polyacrylamide gels containing agarose at a nonrestrictive concentration. The concentration of agarose was 0.4%, the cross-linking degree 2.5%, and T was varied from 0 to 10%. Proteins and DNA were run in gels of various compositions. Their mobilities were determined and used to construct Ferguson plots. FIG. 7 of the reference compares Ferguson plots in the gels with and without agarose. An enhanced selectivity of the gels with agarose is evident, as the 1.3 kbp fragment migrated about 8-fold less in the gel with agarose. It should be noted, however, that in the cited publication the DNA was prestained with ethidium bromide (EtBr), in order to allow recording during electrophoresis. Thus, FIG. 7 of the reference shows the mobilities of DNA-EtBr complexes, and not of pure DNA. In the present invention, DNA was always stained after electrophoresis, and thus migration rates relate to pure DNA fragments. Binding of EtBr is known to reduce DNA mobility. In addition, at high gel concentrations, above about 5%, EtBr dissociates from DNA during electrophoresis, which results in aberrant migration rates and diffuse bands. It is therefore not possible to directly compare the results reported in reference 32 with those of the present invention. Moreover, no data on optical properties of the gels were given in the cited reference. Based on the results described in Example 5, the cross-linking degree of 2.5% is not optimal for obtaining a polyacrylamide-Bis gel of enhanced selectivity. It should also be noted that the authors did not mention enhanced selectivity, or better resolving power, in connection with any one of the gels studied.

In a study on the estimation of pore size of polyacrylamide gels using Ferguson plots (reference 33), agarose at 0.5% was added to polyacrylamide-Bis gels having a cross-linking degree of 3%. It was reported that pore size of the gels with agarose was about one half of the pore size of the gels without agarose. There was no indication that optical properties of the gels with agarose were different from those without it. Furthermore, resolving power of various gels was not addressed. It was suggested (reference 33) that the primary determinant of DNA gel mobility is the total acrylamide concentration. In contrast, results of the present invention showed that a minor increase of gel concentration, due to addition of a polymer at a defined ratio to the monomer and cross-linker, can profoundly change electrophoretic mobility of DNA molecules.

REFERENCES

1. Peacock, A. C., and Dingman, C. W. (1968) Biochemistry, 7, 668–674.
2. Bode, H.-J. (1977) Anal. Biochem., 83, 204–210.
3. Horowitz, P. M., Lee, J. C., Williams, G. A., Williams, R. F., and Barnes, L. D. (1984) Anal. Biochem., 143, 333–340.
4. Bode, H.-J. (1976) FEBS Lett., 65, 56–58.
5. Righetti, P. G., Caglio, S., Saracchi, M., and Quaroni, S. (1992) Electrophoresis, 13, 587–595.
6. Asnaghi, D., Giglio, M., Bossi, A., and Righetti, P. G. (1995) J. Chem. Phys., 102, 9736–9742.
7. Righetti, P. G., Brost, B. C. W., and Snyder, R. S. (1981) J. Biochem. Biophys. Methods, 4, 347–363.
8. Gelfi, C., and Righetti, P. G. (1981) Electrophoresis, 2, 213–219.
9. Davis, B. J. (1964) Ann. N.Y. Acad. Sci., 121, 404–427.
10. Righetti, P. G. (1989) J. Biochem. Biophys. Methods, 19, 1–20.
11. Rodbard, D., and Chrambach, A. (1970) Proc. Natl. Acad. Sci. USA 65, 970–977.
12. Tietz, D. (1988) Adv. Electrophoresis 2, 109–169.
13. Wyckoff, M., Rodbard, D., and Chrambach, A. (1977) Anal. Biochem., 78, 459–482.
14. Stellwagen, N. C. (1987) Adv. Electrophoresis, 1, 179–228.
15. Kozulic, B. (1994) Appl. Theoret. Electrophoresis, 4, 117–123.
16. Kozulic, B. (1994) Appl. Theoret. Electrophoresis, 4, 125–136.
17. Kozulic, B. (1994) Appl. Theoret. Electrophoresis, 4, 137–148.
18. Kozulic, B. (1994) Appl. Theoret. Electrophoresis, 4, 149–159.
19. Kozulic, B. (1995) Anal. Biochem., 231, 1–12.
20. Giddings, J. C. (1991) Unified separation science. John Wiley and Sons, Inc., New York.
21. Lai, E., and Birren, B. W. (Eds.) (1990) Electrophoresis of large DNA molecules: Theory and applications. CSH Press, Cold Spring Harbor.
22. Birren, B., and Lai, E. (1993) Pulsed field gel electrophoresis: A practical approach, Academic Press, San Diego.
23. Brassard, E., Turmel, C., and Noolandi, J. (1992) Electrophoresis, 13, 529–535.
24. Ulanovsky, L., Drouin, G., and Gilbert, W. (1990) Nature, 343, 190–191.
25. Desruisseaux, C., and Slater, G. (1996) Electrophoresis, 17, 623–632.
26. Chiari, M., Campoleoni, A., Conti, P., Felli, C., Patrosso, M. C., and Brogren, C. H. (1996) Electrophoresis, 17, 473–478.
27. Barron, A. E., Sunada, W. M., and Blanch, H. W. (1996) Electrophoresis, 17, 744–757.
28. Bode, H.-J. (1979) Z. Naturforsch., 34 c, 512–528.
29. Bode, H.-J. (1980) In Electrophoresis '79 (Radola, B. J., Ed.) W. de Gruyter, Berlin, pp. 39–52.
30. Cai, L. L., Peanasky, J., and Granick, S. (1996) Trends Polym. Sci., 4, 47–51.
31. Gersten, D. M., and Bijwaard, K. E. (1992) Electrophoresis, 13, 282–286.
32. Pospichal, J., Vicchio, D., and Chrambach, A. (1991) Electrophoresis, 12, 247–253.
33. Holmes, D. L., and Stellwagen, N. C. (1991) Electrophoresis, 12, 612–619.

EXAMPLES

Gels were prepared by free radical polymerization using N,N,N',N'-tetramethylethylenediamine (TEMED) and sodium persulfate as initiators. In most cases, 45 $\mu$l of TEMED and 60 $\mu$l (110 mg/ml) of sodium persulfate were added to 20 ml of the monomer plus cross-linker solution. If not indicated otherwise, NAT was used as the monomer and Bis as the cross-linker. The gels were 3 mm thick and 92 mm long. In most instances, a 2 ml aliquot of the polymerizing solution was placed into a 1-cm disposable plastic cuvette for subsequent absorbance measurement of the resulting gel. During polymerization the gels for electrophoresis were covalently fixed to a plastic backing (Gel Bond Film, FMC Corporation). The gels were run in submerged electrophoresis mode, and therefore their ionic composition was adjusted in accordance with the U.S. Pat. No. 5,458,760. For electrophoresis, the SEA 2000 submerged gel electrophoresis apparatus from Guest Elchrom Scientific was used. This apparatus features improved linearity of electric field, buffer recirculation, and temperature control, as disclosed in U.S. Pat. No. 5,259,943. All electrophoresis runs were carried out using a programmable power supply featuring automatic stop after a pre-set time. During most runs, temperature of the running buffer was controlled by means of a temperature probe which was placed in the running buffer. The probe was connected to a circulating water bath (Huber, Germany). After a few overshoots followed by undershoots at the beginning of electrophoresis, the temperature usually stabilized within 1° C. of the set value. Three to four gels were typically run in one electrophoresis apparatus. The gels were stained with ethidium bromide at 0.2–0.4 $\mu$g/ml in water, if not indicated otherwise. The reproducibility of DNA migration rates measured on gels from the same batch was within 5%. When single gels of a defined composition were polymerized and run on different days in different apparati, variations in the mobilities were sometimes larger than 5%.

DNA samples that were run include several commercial markers as well as plasmid digests. The 100 bp ladder and 20 bp ladder were from GenSura Laboratories, the 1 kb ladder was from Life Technologies, and the 50 bp ladder was from Pharmacia. The plasmid pBR322 was digested with HaeIII, MspI or HhaI, in order to provide additional DNA fragments. Lambda DNA digested with HaeII or HaeIII was also applied to some of the gels.

Example 1

Poly(NAT) gels with different amounts of hydroxyethyl cellulose

A 2% solution of HEC (Fluka, P/N 54290, Cellosize 40-W, middle viscosity) was dissolved in 30 mM Trisacetate-EDTA (TAE) buffer, pH 8.0, by stirring on a magnetic stirrer overnight. The solution was filtered through a sintered glass filter, porosity 2. The solution was slightly brownish. The gel composition was 12% T, 2.6% C. The concentration of HEC in the monomer-cross-linker solution was 0.05%, 0.10%, 0.15%, 0.20%, and 0.30%, respectively. The control gel contained no HEC. Absorbance at 600 nm of the gel without HEC was 0.017, and of the gels with HEC it was 0.121, 0.474, 1.020, 1.780 and 2.239, respectively. Spectra of the gels in the 400–800 nm range are shown in FIG. 3. The gels were run at 10 V/cm for 4 h at 20° C. In the gel without HEC, the 60 bp fragment from the 20 bp ladder migrated 7.3 cm, the 100 bp fragment 5.4 cm, the 200 bp fragment 3.2 cm, the 300 bp fragment 2.2 cm, the 500 bp fragment 1.2 cm, and the 1,000 bp fragment 0.5 cm. In the gel with 0.05% HEC, the same fragments migrated 7.1 cm, 5.1 cm, 2.7 cm, 1.5 cm, 0.4 cm, and 0.1 cm, respectively. At 0.1% HEC, the migration distances were 6.9 cm, 4.7 cm, 1.8 cm, 0.7 cm, 0.1 cm, and less than 0.1 cm. In the gel with 0.15% HEC, the migration distances of the 60, 100, 300, and 500 bp fragments were 7.1 cm, 4.6 cm, 1.3 cm, 0.3 cm, and less than 1 mm. At 0.2% HEC, the distances were, 6.9 cm, 4.1 cm, 0.9 cm, 0.2 cm, and less than 0.1 cm. At 0.3% HEC, the same DNA molecules migrated 6.4 cm, 3.6 cm, 0.7 cm, 0.2 cm, and less than 0.1 cm, respectively. Many additional gels were polymerized with this HEC preparation. After running and staining, a high background opacity was often observed, in particular when SYBR Green (Molecular Probes) was used for detecting separated DNA. It was reasoned that the background came from endogenous DNA present in the HEC, and therefore HEC solution was purified as outlined in Example 2.

Example 2

Purification of HEC

A 1% solution of HEC (Fluka) in 15 mM TAE buffer was passed over 100 ml of DEAE-Sepharose CL 6B, packed in a column of 5 cm diameter, at a flow rate of about 40 ml/h. The ion exchanger was first equilibrated in the same buffer. The exchanger bound the brownish impurity present in the HEC preparation. When this HEC solution was used, the gels showed a negligible background staining. However, the gels almost completely lost their resolving power, as the DNA fragments migrated as a smear, especially in the lower size range. The HEC solution purified over DEAE-Sepharose was then passed through another column, with a diameter of 5 cm, filled with 100 ml of CM-Sepharose, packed in the column. After this second chromatography, purified HEC was added to NAT-Bis solutions. Resolving power of gels was restored. The above result indicates that minute quantities of cationic polymers released from DEAE-Sepharose are able to abolish the resolving power of electrophoresis gels. The released polymers are bound by the cationic ion exchanger, CM-Sepharose. HEC preparations of higher molecular weight were purified in the same manner, only the polymer concentration was lowered to reduce the viscosity. Many gels were polymerized with purified HEC. They consistently showed less background. The overall improvement of selectivity obtained with purified HEC was similar to that obtained with the HEC which was not subjected to the purification procedure described above. Gels containing 0.2% of purified HEC exhibited a particularly high enhancement of selectivity. They were run under a variety of electrophoresis condition. For example, when a 12% T, 2.6% C gel with 0.2% HEC was run at 10 V/cm for 2.5 h at 60° C., migration distances of the 100, 200, 300, 400, and 500 bp fragments were 8.5 cm, 3.2 cm, 1.1 cm, 0.4 cm, and 0.2 cm, respectively.

Example 3

Poly(NAT) gels of equal 12% T, and varying degrees of cross-linking, containing the same amount of purified HEC.

Three poly(NAT) gels were prepared with 0.2% HEC, and 1%, 1.5% and 2.0% Bis. Another three gels contained the same monomer and cross-linker concentrations but no HEC. The absorbance at 600 nm of the three control gels was below 0.010, whereas the absorbance was higher with the gels containing 0.2% HEC. At 1% Bis it was 0.103, at 1.5% Bis the absorbance was 0.321, and at 2.0% Bis it was 0.720. The gels were electrophoresed at 10 V/cm for 4 h at 20° C. In both gels with 1% C, the 154 bp and 3,054 bp fragments from the 1 kb migrated essentially the same distance. In the 1.5% C gel with HEC, the 100 bp fragment from the 100 bp ladder and 3,054 bp band from the 1 kb ladder migrated about 10% less than in the control gel without HEC. Migration rate of the 100 bp fragment was less than 10% lower in the 2.0% C gel with HEC than in the corresponding gel without HEC, but the 3,054 bp fragment migrated less than half the distance in the gel with HEC compared to the gel without HEC. In all these gels, the DNA bands were less sharp than in the gels with 2.6% C. Visible spectra, from 400 nm to 800 nm, were recorded with the gels containing HEC and characterized by a cross-linking degree of 1.5% and 2.0%. Absorbance at 400 nm of the latter gel was about twice as high compared to that at 600 nm, and at 800 nm it was about half of the value measured at 600 nm.

Example 4

Poly(NAT) gels containing HEC and cross-linkers other than Bis

Six 12% poly(NAT) gels were prepared with 1,2-dihydroxyethylene-bis-acrylamide (DHEBA, purchased from Fluka) as the cross-linker. The gels contained 3%, 4%, and 5% C, with and without 0.2% HEC, respectively. The absorbance at 600 nm of the gel with 3% C was 0.018, of the 4% C gel it was 0.031, and of the 5% C gel it was 0.076. The corresponding gels with 0.2% HEC had absorbances of 0.320, 0.755 and 1.302. The gels were run at 10 V/cm for 4 h at 20° C. At 3% C, DNA bands were much sharper in the gel which contained 0.2% HEC. The 200 bp fragment from the 100 bp ladder migrated about 30% less in the gel with HEC. The 3,054 bp band migrated less than one half the distance compared to the gel without HEC. At 4% C, the 100 bp fragment migrated essentially the same distance. The 3,054 bp fragment was clearly resolved in the gel without HEC, whereas in the gel with HEC it remained in the cluster which hardly migrated. The 587 bp fragment from pBR322/HaeIII digest migrated about 5-fold less (2.4 cm versus 0.5 cm) in the gel with HEC. At 5% C, the 50 bp fragment from 50 bp ladder migrated the same distance in both gels (8.4 cm). The migration distance of the 1,000 bp fragment was 0.7 cm in the gel without HEC, whereas in the gel with HEC this fragment did not migrate at all, that is the DNA remained at the entry point of the sample well. The 587 bp fragment migrated 1.1 cm in the gel without HEC, and 0.1 cm in the gel with HEC.

Six 12% poly(NAT) gels were polymerized with piperazine-di-acrylamide (PDA, purchased from Bio-Rad). The gels contained 1%, 1.5%, and 2%C, with or without 0.2% HEC. The absorbance at 600 nm of the gels without HEC was 0.010, 0.045, and 0.283, respectively. With HEC, the absorbance had the following values: 0.807,1.998, and 2.358. The gels were run at 10 V/cm for 4 h at 20° C. At 1% C, the 100 bp fragment migrated about 7 cm in both gels. The 1,000 bp fragment from the same ladder migrated 1.8 cm in the gel without HEC, and only 0.3 cm in the gel with HEC. At 1.5% C, in the control gel without HEC the 100 bp fragment migrated 6.3 cm, and the 1,000 bp fragment from the same ladder migrated 0.8 cm. In the gel with HEC, the migration distance of the 100 bp fragment was 5.5 cm, and the 1,000 bp fragment did not move out of the sample well. The 587 bp fragment migrated about 1 mm. At 2% C, the differences in relative mobilities of larger DNA fragments in the gels with and without HEC were similar to those at 1.5% C. However, the gel with HEC at 2.0% C had a stronger background, and the bands were more diffuse than in other gels of this series. The visible spectrum of this gel showed a high absorbance, over 2.0, at all wavelengths between 400 and 800 nm.

The above results with DHEBA and PDA demonstrate that gels of enhanced selectivity can be obtained with different cross-linkers.

Example 5
Gels of enhanced selectivity comprising a monomer other than NAT

Four 12% polyacrylamide gels were polymerized with Bis as the cross-linker. The cross-linking degrees were 5 and 6%, and two gels contained 0.2% HEC. The absorbance at 600 nm of the gels without HEC was 0.019 and 0.069 for the 5% and 6% C, respectively. For corresponding gels with HEC, the absorbance was 1.507 and 2.247. The gels were electrophoresed at 10 V/cm for 4 h at 20° C. At 5% C, in the gel without HEC, the 20 bp fragment from the 20 bp ladder was at the bottom of the gel (8.7 cm), whereas the 500 bp fragment from the same ladder migrated 0.5 cm. In the corresponding gel with HEC, migration distance of the 20 bp fragment was 8.6 cm. The 500 bp fragment did not migrate at all. Actually, no fragment larger than 300 bp migrated a noticeable distance. At 6% C, in the gel without HEC the 20 bp fragment migrated 8.4 cm, the 200 bp fragment 0.7 cm, and the 300 bp fragment 0.4 cm. In the gel with HEC, migration distance of the 20 bp fragment was 7.9 cm, while the 200 bp fragment migrated about 1 mm. The 300 bp fragment, as well as the larger ones, did not migrate at all. This gel had a high background, and the DNA bands were more diffuse than in other three gels.

Polyacrylamide gels of a lower percentage, cross-linked with Bis, were also prepared from solutions containing no HEC, or 0.2% HEC. The 9% T gels had a crosslinking degree of 2%, 3%, 4%, 5%, and 6%. The absorbance at 600 nm for the gels without HEC was 0.000, 0.004, 0.017, 0.066, and 0.279, respectively. The following values were measured for the gels with HEC:0.136, 0.466, 1.374, 2.131, and 2.300. All gels were run at 10 V/cm for 4 h at 20° C. At 2% C, the difference in mobilities between the gel with HEC and the gel without HEC was less than 10% for the DNA fragments in the size range from 200 bp to 2,000 bp. At 3% C, in the gel without HEC the 100 bp fragment migrated 8.0 cm, and the 1,000 bp fragment 1.9 cm. In the corresponding gel with HEC, the 100 bp fragment migrated 7.5 cm, and the 1,000 bp fragment 0.1 cm. At 4% C, the 80 bp fragment from 20 bp ladder migrated 7.7 cm, and the 500 bp fragment 1.8 cm. In the gel with HEC, the 80 bp fragment migrated 6.5 cm, and the 500 bp fragment less than 1 mm. At 5% C, migration distance of the 60 bp fragment was 8.1 cm, and that of the 400 bp fragment 1.0 cm. The measured distances in the gel with HEC were 6.1 cm and 0.1 cm for the same two DNA fragments. DNA molecules longer than 500 bp did not migrate at all. At 6% C, the 60 bp fragment migrated 7.1 cm, and the 400 bp fragment 0.3 cm. In the gel with HEC, the 60 bp fragment migrated 5.6 cm, and the 400 bp fragment 0.2 cm. This gel displayed a strong background, and the DNA bands were rather diffuse. The visible spectrum was characterized by high absorbance values (above 2.0) over the whole 400–800 nm range.

Another monomer, N-acryloyl-1-amino-1-deoxy-D-galactitol, was also polymerized with Bis as the cross-linker. The 9% T and 3% C gel had an absorbance at 600 nm of 0.009. The gel of the same T and C but containing 0.1% hydroxyethyl cellulose of molecular weight 90,000–105,000 (the molecular weight specified by the supplier, Polysciences, with the HEC purified as described in Example 2), had the absorbance of 0.873. Both gels were run at 10 V/cm for 4 h at 20° C. In the gel without HEC, the 300 bp fragment migrated 8.1 cm, the 500 bp fragment 6.1 cm, the 1,000 bp fragment 3.9 cm, and the 5,090 bp fragment 1.1 cm. In the gel with HEC, the 300 bp fragment migrated 5.6 cm, the 500 bp fragment 2.1 cm, the 1,000 bp fragment 0.2 cm, whereas the 5,090 bp fragment remained in a cluster spreading about 3 mm from the sample well.

Example 6
Gels of enhanced selectivity comprising more than one monomer and more than one cross-linker Four composite gels, containing NAT and acrylamide as the monomers, and Bis as the cross-linker, were prepared. Two gels contained 10% NAT and 2% acrylamide (AA), and the other two 11% NAT and 1% M. The cross-linking degree was 2.6% in all gels. One of each composite gels contained 0.2% of purified HEC. The absorbance at 600 nm of the 10% NAT-2% AA gel was 0.010, and of the corresponding gel with HEC 1.173. Absorbance of the 11% NAT 1% AA gel was 0.013, and of the gel with HEC it was 1.129. All gels were run at 10 V/cm for 4 hat 20° C. In the control 10% NAT-2% AA gel, the 40 bp DNA fragment migrated 8.5 cm, and the 1,000 bp fragment 1.3 cm. In the gel with HEC, the 40 bp fragment migrated 8.6 cm, whereas the 1,000 bp fragment migrated 1 mm. In the control 11% NAT-1% M gel, migration distance of the 60 bp fragment was 7.7 cm, and of the 1,000 bp fragment 1.3 cm. In the gel with HEC, the 60 bp fragment migrated 7.8 cm, while the 1,000 bp fragment migrated 0.1 cm.

Composite gels containing two different cross-linkers were also prepared. One 12% poly(NAT) gels containing 3% DHEBA and 1% Bis was polymerized without HEC, and the other with 0.2% HEC. Absorbance at 600 nm of the gel without HEC was 0.041, and of the gel with HEC 1.835. Both gels were run at 10 V/cm for 4 h at 20° C. In the gel without HEC, the 60 bp DNA fragment migrated 7.6 cm, the 500 bp fragment 1.6 cm, and the 1,000 bp fragment 0.8 cm. In the gel with HEC, the 60 bp fragment migrated 7.4 cm, the 500 bp fragment 0.1 cm, whereas the 1,000 bp fragment remained essentially at the entrance point.

Example 7
Gels of enhanced selectivity containing HEC of different molecular weight Four preparations of HEC were used, with molecular weights of 24,000–27,000 (specified by the producer, Polysciences, P/N 05570), an HEC of middle viscosity (Fluka, purified as described in Example 2), an HEC of molecular weight of 90,000–105,000 (Polysciences, P/N 05569, purified), and an HEC of high molecular weight (Polysciences, P/N 05568). In the first series, 9% Poly (NAT), 2.6% Bis gels were prepared with varying amounts of different HEC preparations. The gels were run at 10 V/cm for 4 h at 20° C. Four gels contained HEC 24,000–27,000, at 0.1%, 0.2%, 0.3% and 0.4%. Absorbance values at 600 nm were 0.068, 0.214, 0.521, and 0.995, respectively, while the control gel without HEC had the absorbance of 0.023. In the control gel, the 140 bp fragment from the 20 bp ladder migrated 8.3 cm, the 500 bp fragment 3.4 cm, and the 1,000 bp fragment 1.6 cm. In the gel with 0.1% HEC (24,000–27, 000), the 140 bp fragment migrated 7.5 cm, the 500 bp fragment migrated 2.6 cm, and the 1,000 bp fragment migrated 1.3 cm. In the gel with 0.2% HEC, the migration distances of the three fragments were 7.4 cm, 2.0 cm, and 0.8 cm. In the gel with 0.3% HEC, the migration distances were 7.2 cm, 1.7, and 0.5 cm. In the gel with 0.4% HEC, the migration distances were 6.8 cm, 1.5, and 0.5 cm. The gels with 0.3% and 0.4% HEC showed a high background. From the above migration distances it is clear that the selectivity changed very little, although opacity of the gels varied substantially.

Three gels, of 9% T and 2.6% C, were polymerized from solutions containing 0.1%, 0.15%, and 0.2% of another HEC (from Fluka). The absorbance values at 600 nm were 0.389, 0.883, and 1.509. The migration distances of 140 bp, 500 bp, and 1,000 bp fragments were 8.3 cm, 3.4 cm, and 1.6 cm, respectively. In the gel with 0.1% HEC, the migration distances were 7.5 cm, 1.3 cm, and 0.2 cm. In the gel with 0.15% HEC, the distances were 7.0 cm, 0.7 cm, and less than 0.1 cm. In the gel with 0.2% HEC, the 140 bp fragment migrated 6.7 cm, and the 500 bp fragment migrated 0.5 cm. DNA fragments longer than 800 bp remained in a cluster which migrated less than 1 mm.

Six gels, of 9% T and 2.6% C, were prepared from solutions which contained 0.02%, 0.04%, 0.06%, 0.08%, 0.10%, and 0.15% of the HEC having molecular weights of 90,000–105,000. The absorbance of these gels at 600 nm was 0.151, 0.480, 0.942, 1.392, 1.438 and 1.903. The gels were run at 10 V/cm for 4 h at 20° C. In the control gel, whose absorbance at 600 nm was 0.023, the 140 bp DNA fragment migrated 8.3 cm, the 300 bp fragment migrated 5.1 cm, the 500 bp fragment migrated 3.4 cm, and the 1,000 bp fragment migrated 1.6 cm. In the gel with 0.02% HEC, the 140 bp fragment migrated 6.6 cm, the 500 bp fragment migrated 0.4 cm, and the 1,000 bp fragment did not migrate a measurable distance. In the gel with 0.04% HEC, the 140, 300, and 500 bp fragments migrated 5.7 cm, 1.1 cm, and 0.2 cm, respectively. In the gel with 0.06% HEC, the migration distances of the same three fragments were 5.0 cm, 0.7, and 0.1 cm. In the gel with 0.08% HEC, the migration distances were 5.2 cm, 0.8 cm, and 0.1 cm. In the gel with 0.1% HEC, the 140 bp DNA fragment, the 300 bp fragment, and the 500 bp fragment migrated 7.5 cm, 2.6 cm, and 0.6 cm, respectively. In the gel with 0.15% HEC, the three fragments migrated 6.8 cm, 3.1 cm, and 0.9 cm, respectively. Mobilities of the longer DNA fragments thus increased when the HEC concentration was raised above a certain value. The enhanced selectivity observed at 20° C. was also noticed in the gels that were run at a high temperature. For example, in the gel with 0.04% HEC run at 10 V/cm for 2.5 h at 55° C., the 200 bp DNA fragment migrated to the gel end, while the 1,000 bp fragment migrated less than 2 mm.

Four gels were prepared with HEC of high molecular weight (Polysciences), containing 0.02%, 0.04%, 0.1% and 0.2% of the polymer. The absorbance values measured at 600 nm were 0.166, 0.501, 1.765, and 2.037. The gels were electrophoresed at 10 V/cm for 4 h at 20° C. Compared to the 9% T, 2.6% C gel without HEC, there was a pronounced retardation of larger molecules in the gels with HEC. Thus, in the gel with 0.02% HEC, the migration distances of the DNA fragments of 140 bp, 300 bp, 500, and 1,000 bp were 8.1 cm, 3.8 cm, 1.1 cm, and 0.1 cm, respectively. At 0.04% HEC, the migration distances were 7.4 cm, 2.4 cm, 0.4 cm, and less than 1 mm. At 0.1% HEC, the distances were 6.8 cm, 1.3 cm, 0.4 cm, and less than 1 mm. At 0.2% HEC, the fragments of 140 bp, 300 bp, 500 bp, and 1,000 bp migrated 8.0 cm, 4.3 cm, 1.9 cm, and 0.3 cm, respectively. Thus, the mobilities increased again at a higher HEC concentration. The gel with 0.2% HEC had a high background, and the DNA bands were rather diffuse.

In addition to the 9% T, 2.6% C poly(NAT) gels described above, 12% T, 2.6% C gels with HEC of different molecular weights were also prepared. Gels of other cross-linking degrees were polymerized as well. The same general pattern was observed. DNA mobilities decreased in relation to the amount of HEC present in the polymerizing solution. The retardation effect was more pronounced with HEC polymers having a higher molecular weight.

Example 8

Poly(NAT) gels of lower percentages showing enhanced selectivity

Four 6% poly(NAT) gels were prepared which contained Bis as the cross-linker at 2.6% C. Three of them had HEC, of molecular weight 95,000–105,000, at different concentrations, 0.05%, 0.10%, and 0.2%. All four gels were run at 7 V/cm for 4 h at 20° C. In the control gel, the 220 bp DNA fragment from 20 bp ladder migrated 8.6 cm, the 1,000 bp fragment from the same ladder migrated 3.5 cm, and the 3,054 bp fragment from 1 kb ladder migrated 1.7 cm. The 5,090 band from this ladder was clearly resolved from other bands. In the gel with 0.05% HEC, the 220 bp fragment migrated 7.5 cm, the 1,000 bp fragment migrated 0.5 cm, and the 3,054 bp fragment migrated less than 0.3 cm. This fragment, as well as all others larger than 2,000 bp, remained unresolved in a cluster whose front migrated 3 mm. In the gel with 0.1% HEC, the 220 bp fragment migrated 7.3 cm, the 1,000 bp fragment migrated 0.9 cm, while the 3,054 band was not resolved. In the gel with 0.2% HEC, the 220 bp fragment migrated 8.0 cm, the 1,000 bp fragment migrated 2.9 cm, and the partially resolved 3,054 bp fragment migrated 1.1 cm. The longer migration distances in this gel were accompanied by more diffuse bands, especially in the size range above 1,000 bp. Thus, an increase of the HEC concentration above certain level also led to faster DNA migration in 6% poly(NAT) gels.

In Example 7, the gels of enhanced selectivity were about 9% in dry weight, and in the present example such gels were about 6% in dry weight.

Example 9

Gels of enhanced selectivity containing other cellulose polymers

Four 12% T, 2.6% C gels were prepared with methyl cellulose (MC, Fluka, P/N 64620) at the following concentrations: 0.05%, 0.10%, 0.15%, and 0.20%. The absorbance at 600 nm was 0.225, 0.757, 1.533 and 2.053, respectively. The gels were run at 10 V/cm for 4 h at 20° C. In the gel with 0.05% MC, mobilities of the 60, 100, 300, 500, and 1,000 bp DNA fragments were 7.5 cm, 5.9 cm, 2.8 cm, 1.5 cm, and 0.6 cm, respectively. At 0.1% MC, the same molecules migrated 6.8 cm, 5.6 cm, 1.9 cm, 0.6 cm, and 0.1 cm. At 0.15% MC, the fragments migrated 6.5 cm, 5.4 cm, 0.9 cm, 0.2 cm, and less than 1 mm. At 0.2% MC, migration distances of the 60, 100, 300 and 500 bp fragments were 6.8 cm, 4.9 cm, 0.8 cm, and 0.2 cm respectively.

Four gels of 12% T and 2.6% C were prepared with hydroxypropyl-methyl cellulose (HPMC, Aldrich, P/N 29,441-1) as the preformed additive polymer. Its concentration was 0.05%, 0.10%, 0.15%, and 0.20%. The absorbance at 600 nm of the gels polymerized in 1 cm cuvettes was 0.052, 0.215, 0.524, and 1.006, respectively. The gels were electrophoresed at 10 V/cm for 4 h at 20° C. In the gel with 0.05% HPMC, migration distances of the 60, 100, 300, 500, and 1,000 bp fragments were 7.5 cm, 5.8 cm, 2.9 cm, 1.8 cm, and 0.9 cm, respectively. At 0.1% HPMC, the distances were 7.5 cm, 5.8 cm, 2.6 cm, 1.4 cm, and 0.5 cm. At 0.15%, the same fragments migrated 7.3 cm, 5.6 cm, 2.2 cm, 0.9 cm, and 0.2 cm. In the gel with 0.2% HPMC, the five fragments migrated 7.4 cm, 5.7 cm, 1.7 cm, 0.5 cm, and 0.1 cm.

Example 10

Gels of enhanced selectivity containing agarose and derivatized agaroses

Three gels of 12% T and 2.6% C were polymerized from solutions containing different concentrations of agarose (Serva, P/N 11401). The agarose was first dissolved by boiling in 30 mM TAE buffer at 1% concentration. After cooling to about 60° C., appropriate amounts of this solution were mixed with the monomer and cross-linker solution to give 0.1%, 0.15%, and 0.2% final agarose concentration. The three gels were run at 10 V/cm for 4 h at 20° C. At 0.1% agarose, the 60 bp DNA fragment migrated 8.3 cm, the 100 bp fragment migrated 5.5 cm, the 200 bp fragment migrated 1.2 cm, the 300 bp fragment migrated 0.2 cm, and longer DNA molecules hardly migrated at all. In the gel with 0.15% agarose, the same fragments migrated 7.5 cm, 4.6 cm, 0.8 cm, and 0.2 cm, respectively. At 0.2% agarose, the migration distances of the 60, 100, 200, and 300 bp fragments were 8.0 cm, 5.0 cm, 1.3 cm, and 0.4 cm, respectively.

SeaPlaque agarose (FMC Corporation) was used as the polymer in combinations with NAT and Bis. When a 12% T, 2.6% C gel containing 0.05% SeaPlaque agarose was electrophoresed at 10 V/cm for 4 h at 20° C., migration distances of the 60 bp, 100 bp, 200 bp and 300 bp fragments were 7.3 cm, 5.6 cm, 2.6 cm, and 0.8 cm, respectively. At 0.1% SeaPlaque agarose, the migration distances were 7.3 cm, 4.6 cm, 0.6 cm, and 0.1 cm. In the gel with 0.2% SeaPlaque agarose, the 60 bp fragment migrated 6.5 cm, the 100 bp fragment migrated 2.9 cm, and the 200 bp fragment migrated 0.2 cm. DNA molecules larger than 300 bp migrated less than 1 mm.

Gels of the same T and C as above, containing 0.2% SeaPlaque agarose, were polymerized in batches of 6 at different temperatures of the polymerization solution, from 15° C. to 35° C. The polymerizing solution became slightly opaque at 15° C. before the gel was formed. DNA bands were less sharp in this gel than they were in the gels polymerized at higher temperatures. The gels polymerized at 35° C. were less opaque than those which were polymerized at lower temperatures. Regardless of the polymerization temperatures, all gels showed enhanced selectivity, such that the 500 bp fragment migrated less than 0.3 cm in all gels. However, band sharpness and the extent of selective retardation were different, being the highest for the gels polymerized at 35° C. The gels were run also at elevated temperatures, from 30° C. to 62° C. There was a significant difference in mobilities of DNA fragments larger than 300 bp between the gel polymerized at 20° C. and 35° C., when run at 60° C. The mobilities were higher in the gel polymerized at 20° C. In the gel polymerized at 35° C., the 104 bp fragment from pBR322/MspI was at the gel bottom whereas the 622 bp fragment migrated about 1 mm, after a 2.5 h run at 62° C. at 10 V/cm.

A 12% T, 2.6% C gel with 0.2% SeaPlaque agarose was polymerized between two glass plates (gel thickness 0.7 mm), and run in a vertical format using the Pharmacia GE-2/4 apparatus. Enhanced selectivity was also observed in this gel, similar to the enhanced selectivity seen in submerged gels of the same composition.

Another derivatized agarose, NuSieve (FMC Corporation), was also used as the polymer in 12% T, 2.6% C poly(NAT)-Bis gels. Its concentrations in the polymerizing solution were 0.05%, 0.1%, 0.15%, 0.2%, 0.3%, 0.4% and 0.5%. All gels were run at 10 V/cm for 4 h at 20° C. In the gel with 0.05% NuSieve agarose, the 60 bp fragment migrated 8.0 cm, the 100 bp fragment 6.2 cm, the 200 bp fragment 4.0 cm, the 300 bp fragment 2.9 cm, the 500 bp fragment 1.7 cm, and the 1,000 bp fragment 0.9 cm. In the gel with 0.1% NuSieve agarose, the same fragments migrated 8.2 cm, 6.2 cm, 3.8 cm, 1.3 cm, and 0.6 cm, respectively. At 0.15% of the polymer, the distances were 8.2 cm, 6.0 cm, 3.1 cm, 1.7 cm, 0.6 cm, and 0.2 cm. At a concentration of 0.2% NuSieve agarose, the DNA molecules of 60, 100, 200, 300 and 500 bp migrated 7.1 cm, 5.0 cm, 1.7 cm, 0.4 cm, and 0.1 cm, respectively. At 0.3% of the polymer, migration distances of the 60, 100 and 200 bp fragments were 6.8 cm, 3.5 cm, and 0.4 cm, respectively. All larger DNA molecules migrated less than 0.2 cm. At 0.4% of NuSieve agarose, migration distances of the three DNA molecules were 6.6 cm, 3.0 cm, and 0.2 cm, respectively, whereas at a concentration of 0.5% NuSieve agarose, they migrated 5.8 cm, 2.3 cm, and 0.1 cm, respectively.

There was a significant difference in the behavior of the gels containing SeaPlaque agarose and NuSieve agarose when electrophoresed at elevated temperatures. The retardation of larger molecules was greatly reduced in the gels with NuSieve agarose, such that the 500 bp fragment migrated 2.7 cm in the gel with 0.3% NuSieve agarose run at 10 V/cm for 3 h at 65° C.

The third derivatized agarose, SeaPrep (FMC Corporation), was also used in combination with NAT and Bis. The 12% T, 2.6% C gels contained 0.05%, 0.1%, 0.15%, 0.2%, 0.25%, 0.3% and 0.4% of the SeaPrep agarose. They were run at 10 V/cm for 4 h at 20° C. In the gel with 0.05% SeaPrep agarose, migration distances of the 60, 100, 200, 300, 500, and 1,000 bp DNA fragments were 8.4 cm, 6.6 cm, 4.1 cm, 2.9 cm, 1.6 cm, and 0.7 cm, respectively. In the gel with 0.1% of the polymer, the same fragments migrated 8.2 cm, 6.1 cm, 3.4 cm, 1.9 cm, 0.7 cm, and 0.2 cm. At 0.15% SeaPrep agarose, the migration distances were 8.0 cm, 5.8 cm, 2.5 cm, 1.0 cm, 0.3 cm, and less than 0.1 cm. At 0.2% of the polymer, the 60, 100, 200, and 300 bp fragments migrated 7.7 cm, 5.4 cm, 1.7 cm, and 0.5 cm, respectively. At 0.25%, the same four fragments migrated 7.5 cm, 4.9 cm, 1.2 cm, and 0.3 cm. At 0.3%, the migration distances were 7.4 cm, 4.6 cm, 0.9 cm, and 0.3 cm, whereas at 0.4% they were 7.1 cm, 4.3 cm, 0.9 cm, and 0.3 cm. In the last gel, the DNA bands were rather diffuse and the gels showed a high background.

Example 11

Gels of enhanced selectivity containing other polysaccharides

Four 12% T, 2.6% C gels were polymerized in the presence of varying amounts of dextran of 500,000 molecular weight (Fluka, P/N 31392). The gels contained 0.4%, 0.6%, 0.8%, and 1.0% of the dextran. Absorbance at 600 nm of the gels, polymerized as usual in 1 cm cuvettes, was 0.345, 0.779, 1.639, and 2.167, respectively. The gels were run at 10 V/cm for 4 h at 20° C. In the gel with 0.4% dextran, migration distances of the 60, 100, 200, 500, and 1,000 bp fragments were 7.3 cm, 5.2 cm, 2.3 cm, 0.4 cm, and less than 1 mm, respectively. At 0.6% dextran, the migration distances were 7.2 cm, 4.9 cm, 1.9 cm, 0.3 cm, and less than 0.1 cm. In the gel with 0.8% dextran, the same fragments migrated 6.9 cm, 4.5 cm, 1.6 cm, 0.3 cm, and less than 0.1 cm. At 1.0% dextran, the fragments migrated 6.7 cm, 4.4 cm, 1.8 cm, 0.4 cm, and 0.1 cm. Thus, mobilities of the 300–1,000 bp fragments increased slightly in the gel with 1.0% dextran. The DNA bands were rather diffuse in this gel, and also the background was more pronounced.

Locust bean gum (Sigma, P/N G-0753) was also used as the preformed polymer present during polymerization of NAT-Bis gels at T=12%, and C=2.6%. The crude polymer, at 0.5%, was partially dissolved by boiling in 30 mM TAE buffer, and the cloudy solution was filtered through a sintered glass filter (porosity 4). The clear filtrate became cloudy again upon standing. Concentration of this polymer in the gels was 0.02%, 0.03%, 0.05%, 0.1%, and 0.15%, assuming that there were no losses during dissolution and filtration. Absorbance at 600 nm of the gels was 0.076, 0.147, 0.372, 1.240, and 1.811, respectively. The gels were run at 10 V/cm for 4 h at 20° C. In the 12% T, 2.6% C control gel, DNA fragments of 60, 100, 200, 300, 500, and 1,000 bp migrated 8.0 cm, 6.2 cm, 4.2 cm, 3.1 cm, 1.9 cm, and 1.0 cm, respectively. At 0.02% locust bean gum, the same fragments migrated 7.5 cm, 5.7 cm, 3.2 cm, 1.6 cm, 0.3 cm, and less than 0.1 cm. At 0.03%, the migration distances were 7.4 cm, 5.5 cm, 2.7 cm, 1.0 cm, 0.1 cm, and less than 0.1 cm. At 0.05% of locust bean gum, the specified DNA fragments migrated 8.4 cm, 6.4 cm, 3.1 cm, 1.1 cm, 0.2 cm, and less than 0.1 cm. In this gel, background staining was pronounced and DNA bands were rather diffuse, in particular those below 200 bp. In the gel which contained 0.1% of locust bean gum, all DNA bands below 300 bp were very diffuse and the gel resolving power was greatly diminished. The DNA fragments larger than 500 bp hardly migrated, and the background was strong. At 0.15% locust bean gum, resolution was completely lost in the region below about 300 bp, all bands were diffuse, and the background was strong. The 500 bp fragment migrated 0.3 cm.

Another galactomannan (carubin type, Senn Chemicals, P/N 24024) was also tested. The polysaccharide was dissolved at a concentration of 0.2% by boiling in 30 mM TAE buffer. Four 12% T, 2.6% C gels were prepared which contained 0.01%, 0.02%, 0.03%, and 0.04% of the polymer, respectively. Absorbance at 600 nm of the four gels was 0.079, 0.218, 0.431, and 0.697, respectively. The gels were electrophoresed at 10 V/cm for 4 h at 20° C. In the control gel, whose absorbance was 0.023, the 60 bp fragment migrated 7.1 cm, the 100 bp fragment 5.2 cm, the 200 bp fragment 3.0 cm, and the 500 b fragment 1.1 cm. In the gel with 0.01% of the galactomannan, the same fragments migrated 7.0 cm, 4.9 cm, 2.2 cm, and 0.1 cm. At 0.02% galactomannan, the migration distances were 6.9 cm, 4.6 cm, 1.2 cm, and less than 0.1 cm. At 0.03% galactomannan, the fragments migrated, 6.8 cm, 4.2 cm, 0.8 cm, and less than 1 mm. At 0.04% of the galactomannan polymer, the 60 bp, 100 bp, and 200 bp fragments migrated 6.9 cm, 4.1 cm, and 0.7 cm, respectively.

Example 12

Gels of enhanced selectivity containing more than one polymer

A batch of six 12% T, 2.6% C gels was polymerized with a mixture of purified HEC (Fluka) and SeaPlaque agarose, such that the final concentrations of HEC and agarose were 0.15% and 0.1%, respectively. One gel was run at 10 V/cm for 3 h at 40° C. Under these conditions, the 60 bp DNA fragment migrated out of the gel, while migration distances of the 80, 100, 200, 300 bp fragments were 7.6 cm, 5.8 cm, 1.2 cm, and 0.3 cm, respectively. Fragments larger than 500 bp hardly migrated. Another gel was run at 10 V/cm for 2.5 h at 60° C. The fragments of 100, 200, 300, and 500 bp migrated 8.5 cm, 2.8 cm, 0.9 cm, and 0.2 cm, respectively. In the pBR322/HhaI digest, the 131 and 132 bp fragments were resolved.

Example 13

Gels containing polyethylene glycol (PEG), polyvinyl alcohol (PVA), and polyvinylpyrrolidone (PVP)

Two preparations of PEG of different molecular weight were tested, one of 4,000 (Merck), and the other of 8,000 (Sigma). With 12% T, 2.6% C gels and the PEG 4,000, there was little change of absorbance at 600 nm with increasing PEG concentrations. The gel with 2% PEG had an absorbance of 0.073. At the same T and C, the gel which contained 2% of PEG 8,000 had an absorbance of 0.400. Both gels, together with a gel without PEG, were run at 10 V/cm for 4 h at 20° C. Migration distances of the 100, 200, 500, and 1,000 bp fragments in the PEG 4,000 gel were 7.2 cm, 5.0 cm, 2.4 cm, and 1.2 cm, respectively. In the gel with 2.0% of PEG 8,000, the same fragments migrated 7.7 cm, 5.6 cm, 2.7 cm, and 1.3 cm. The DNA bands were more diffuse in the latter gel, and the gel showed a high background. In the control gel, the migration distances were 7.0 cm, 4.9 cm, 2.4 cm, and 1.3 cm. The mobilities of the DNA fragments thus changed only by 10–20% after the addition of PEG to the polymerization solutions.

Two gels of 12% T and 2.6% C were polymerized in the presence of PVP of 360,000 molecular weight (Sigma). One gel contained 0.2%, and the other 0.5% of the PVP. No change in gel opacity was observed visually. The gels were run at 10 V/cm for 4 h at 20° C. At 0.2% PVP, migration distances of 100, 200, 500, and 1,000 bp fragments were 7.0 cm, 4.8 cm, 2.2 cm, and 1.2 cm, respectively. At 0.5% PVP, the distances were 5.9 cm, 4.1 cm, 1.9 cm, and 1.0 cm. Thus, there was a slight retardation effect in the gel with 0.5% PVP, but the selectivity was not improved since both small and large DNA fragments were retarded to a similar extent. In the gel with 0.5% PVP, bromphenolblue tracking dye migrated only about one third compared to the control gel.

Polyvinyl alcohol (PVA) of 22,000 molecular weight (Fluka, P/N 81382) was added to four 12% T, 2.6% C gels, so that its concentration was 0.2%, 0.4%, 0.6%, and 0.8%. Absorbance at 600 nm of the control gel was 0.011, and of the gels with increasing amounts of PVA 0.017, 0.026, 0.042, and 0.064. At 400 nm, the absorbance values of the same five gels were 0.059, 0.081, 0.119, 0.181, and 0.271, respectively. At 800 nm, the following values were measured: 0.005, 0.007, 0.010, 0.016, and 0.024. Compared to the control gel, absorbance of all gels with PVA was higher but, interestingly, the ratio of absorbance at 400 and 800 nm remained essentially constant in all gels. With other polymers, the ratio decreased with polymer concentration. The gels were run at 10 V/cm for 4 h at 20° C. In the control gel, the 60 bp fragment migrated 7.0 cm, and the 1,000 bp fragment 1.1 cm. At 0.2% PVA, the two fragments migrated 6.9 cm, and 1.2 cm, respectively. At 0.4% PVA, the migration distances were 6.9 cm and 1.4 cm. At 0.6% concentration, the two fragments migrated 6.9 cm and 1.6 cm, respectively. In the gel with 0.8% PVA, the 60 bp fragment migrated 7.2 cm, and the 1,000 bp fragment 1.9 cm. Thus, PVA caused a decrease of gel selectivity, even though the absorbance at 600 nm was higher than in the control gel. DNA bands were also more diffuse in the gels with PVA.

Example 14

Gels of enhanced selectivity which contain polyacrylamide

Four 12% T, 2.6% C gels were polymerized in the presence of polyacrylamide (PAA) having a molecular weight of 10,000 (Polysciences, P/N 17271). This polymer was used at the following concentrations: 0.05%, 0.10%, 0.15%, and 0.2%. The absorbance at 600 nm of the gels polymerized in cuvettes was 0.320, 0.862, 1.375, and 1.732, respectively. The gels were run at 10 V/cm for 4 h at 20° C. In the gel which contained 0.05% PAA, the fragments of 60, 100, 200, 300, and 500 bp migrated 6.6 cm, 4.5 cm, 1.0 cm, 0.2 cm and less than 0.1 cm, respectively. At 0.1% PAA, the fragments migrated 6.7 cm, 4.1 cm, 0.7 cm, 0.2 and less than 0.1 cm. At 0.15% PAA, the shortest four fragments migrated 6.7 cm, 3.9 cm, 0.6 cm, and 0.1 cm. At 0.2% PAA, migration distances were 7.0 cm, 4.2 cm, 1.0 cm, and 0.3 cm. Thus, the mobilities were higher in the gel which contained 0.2% PAA than in the gel with 0.15% PAA.

Example 15

Gels of enhanced selectivity in which the polymer comprises the same monomer as the gel Poly(NAT) was prepared by polymerizing 100 ml of the 5% NAT monomer in 80 mM TAE, under argon with stirring for about 45 min. The resulting polymer was added to solutions containing NAT and Bis. In one series, the initial concentration of NAT was 9%, with 2.6% C, and the solutions also contained, assuming that the above polymerization was 100% complete, 0.5%, 1% and 2% of poly (NAT). As a control, NAT monomer was added instead of the polymer at 0.5%, 1%, and 2%, respectively. Thus, the final T values were 9.5%, 10%, and 11%. The C values decreased as the added monomer, or the polymer, diluted the cross-linker. The absorbance at 600 nm of the gels without poly(NAT) was negligible, whereas the absorbance of the gel with 0.5% poly(NAT) was 1.063, of the gel with 1% 1.922, and with 2% poly(NAT), it was 2.093. All gels were run at 10 V/cm for 4 h at 20° C. In the 9.5% gel made without added poly(NAT), the 120 bp fragment migrated 8.7 cm, the 220 bp fragment migrated, 6.5 cm, the 1,000 bp fragment 2.3 cm, whereas the 5,090 bp fragment migrated 0.8 cm. In the 9.5% gel with 0.5% poly(NAT), the 120 bp fragment migrated 5.2 cm, the 220 bp fragment 1.3 cm, and all molecules larger than 500 bp hardly migrated (less than 1 mm). The migration distances measured in the gel of 10% T without added polymer were only slightly lower than in the gel with 9.5% T, and again decreased slightly at 11% T. In the 10% T gel with 1% added poly(NAT), the mobilities of DNA fragments were higher than in the 9.5% T gel with 0.5% added poly(NAT). For example, the 120 bp fragment migrated 5.8 cm, and the 220 bp fragment 3.1 cm. DNA molecules of 500 bp migrated about 0.7 cm. In the gel with 2% added poly(NAT), there was a further increase of mobilities of all DNA fragments, so that the 1,000 bp fragment migrated about 1.3 cm. The gels at 1% and 2% added polymer had a high background, and the DNA bands were more diffuse than in the gel with 0.5% added poly(NAT).

Example 16

Gels of enhanced selectivity electrophoresed under denaturing conditions

Poly(NAT) gels were polymerized in the presence of 6M urea. Five 12% T, 2.6% C gels were prepared with 0%, 0.15%, 0.2%, 0.3%, and 0.4% of purified HEC (from Fluka). The absorbance of the five gels at 600 nm was 0.000, 0.050, 0.105, 0.295, and 0.562, respectively. The gels were run at 10 V/cm for 2 h at 55° C. in 30 mM TAE buffer containing 6M urea. Under these running conditions, most DNA fragments remained double stranded, as judged by characteristic band patterns of various markers. Some DNA fragments were partially, and some completely denatured, judged by more diffuse bands of certain fragments, and by the absence of other bands from their usual positions. For example, in the 1 kb ladder, the 1,018 bp fragment, the 2,038 and higher molecular weight fragments largely disappeared. In their place there was a smear which migrated only a few millimeters. The 517 bp fragment from this ladder also disappeared. In pBR332 digests, with MspI, HaeIII and HhaI, new sharp bands appeared in the high molecular weight region. Identification of these bands was not attempted. In the gel without HEC, the 100 bp fragment from 100 bp ladder migrated 5.9 cm, the 500 bp fragment 2.5 cm, and the 1,000 bp fragment 1.4 cm. In the gel with 0.15% HEC, migration distances of these three fragments were 5.9 cm, 2.4 cm, and 1.3 cm, respectively. At 0.2% HEC, the distances were 5.7 cm, 2.1 cm, and 1.1 cm. At 0.3% HEC, the fragments migrated 5.4 cm, 1.4 cm, and 0.4 cm. In the gel with 0.4% HEC, the three fragments migrated 5.3 cm, 0.8 cm, and 0.3 cm, respectively. Identification of the 1,000 bp band in the last two gels was not certain due to the appearance of multiple new bands in the ladder.

Four 12% T gels of higher cross-linking degree with 0.2% HEC (Fluka) were prepared as well. In two gels the cross-linking degree was 3.4%, and in the other two 4.0%. At both C values, without HEC, the gels had negligible absorbance at 600 nm. The absorbance was 0.263 and 0.483 for the 3.4% and 4.0% C gels, respectively. The gels were run at 10 V/cm for 2 h at 55° C. in 30 mM TAE-6M urea buffer. In the control gel of 3.4% C, the 75 bp fragment from 1 kb ladder migrated 5.9 cm, the 506 bp fragment migrated 1.6 cm, and the 1,636 bp fragment 0.6 cm. In the gel with HEC, the three fragments migrated 5.7 cm, 0.3 cm, and 0.1 cm, respectively. At 4.0% C, in the control gel the migration distances of the 75 bp, 506, and 1,636 bp DNA fragments were 5.2 cm, 1.1 cm, and 0.4 cm, respectively. In the gel with HEC, the 75 bp fragment migrated 4.2 cm, whereas the migration distances of the 506 and 1,636 bp fragments could not be measured, as they were less than 1 mm.

Example 17

Gels of enhanced selectivity prepared with HEC fractionated by gel filtration

A column having a diameter of 5 cm was filled with 500 ml of Sepharose CL 6B, and then equilibrated in 30 mM TAE. A 50 ml sample of 1% HEC (Fluka), purified as described in Example 2, was applied to this column and chromatographed at a flow rate of about 100 ml/h. Fractions of approximately 11.5 ml were collected. Alternate fractions were analyzed for sugar content by the orcinol-sulfuric acid method. The eluate was sugar-positive starting with fraction 18, and sugars could be detected in all subsequent fractions tested, up to the fraction 42. HEC concentration in the fractions was determined from a standard curve prepared with the starting HEC solution. Three gels of 12% T, 2.6% C were prepared with the HEC from different fractions. Fractions 18 and 19 were used for the first gel, 30 and 31 for the second, and 40 and 41 for the third gel. The final concentration of HEC in the three gels was, based on sugar measurement, 0.08%. 0.19%, and 0.08%, respectively. The absorbance at 600 nm was 1.019, 0.455, and 0.028. The gels were electrophoresed at 10 V/cm for 4 h at 20° C. In the gel containing HEC from fractions 18–19, the 60, 100, 200, 500, and 1,000 bp fragments migrated 7.8 cm, 5.6 cm, 2.3 cm, 0.1 cm, and less than 0.1 cm, respectively. In the gel with HEC from fractions 30 and 31, migration distances of the same molecules were 7.8 cm, 6.1 cm, 3.8 cm, 1.1 cm, and 0.3 cm. In the gel which contained HEC from fractions 40 and 41, the same DNA fragments migrated 7.8 cm, 6.2 cm, 4.2 cm, 2.1 cm, and 1.1 cm. The selectivity thus became worse as molecular weight of the HEC polymers decreased.

The foregoing invention has been described in considerable detail. While the experimental results have been interpreted in the way believed to be the most consistent with all current findings, and also with prior art, the explanations should be considered non-limiting in any aspect. It will be apparent to those skilled in the art that modifications and changes may be made in the procedures and materials utilized without departing from the concept and scope of the invention as described in the following claims.

What is claimed is:

1. A gel suited for use in electrophoretic separation of high molecular weight molecules comprising the free radical polymerization reaction product of a mixture of:
    at least one monomer; and
    at least one vinyl cross linker reactive with said monomer and a polymer of said monomer sufficient to cross link said polymer; and
    at least one preformed polymer;
        wherein the concentration of a combination of said monomer and said cross linker is at least about 4% (w/v), and the concentration of said preformed polymer is about 0.005 to 2% (w/v);
        wherein said gel selectively retards the electrophoretic migration rate of larger macro molecules, as compared to the migration rate of smaller macro molecules, from among DNA fragments of about 100 bp to 3,000 bp, by at least 5 fold as compared to the migration rates of the same molecules under the same conditions in a gel of substantially the same concentration and comprising the free radical polymer reaction product of a solution containing identical concentrations of said monomer and said cross linker but in the absence of said preformed polymer, provided that when the monomer is acrylamide, and the cross linker is N,N'-methylene-bis-acrylamide, the preformed polymer is not agarose.

2. A gel of claim 1 comprising one monomer.
3. A gel of claim 2, wherein the monomer is N-acryloyl-tris(hydroxymethyl)aminomethane.
4. A gel of claim 2, wherein the monomer is acrylamide.
5. A gel of claim 2, wherein the monomer is N-acryloyl-1-amino-1-deoxy-D-galactitol.
6. A gel of claim 1, containing more than one monomer.
7. A gel of claim 6, wherein the monomers are acrylamide and N-acryloyl tris(hydroxymethyl)aminomethane.
8. A gel of claim 1 containing one cross-linker.
9. A gel of claim 8, wherein the cross-linker is N,N'-methylene-bis-acrylamide.
10. A gel of claim 8, wherein the cross-linker is dihydroxyethylene-bis-acrylamide.
11. A gel of claim 8, wherein the cross-linker is piperazine-di-acrylamide.
12. A gel of claim 1 containing more than one cross-linker.
13. A gel of claim 12, wherein the cross-linkers are N,N'-methylene-bis-acrylamide and dihydroxyethylene-bis-acrylamide.
14. A gel of claim 1 containing one polymer.
15. A gel of claim 14, wherein the polymer is a polysaccharide.
16. A gel of claim 15, wherein the polymer is hydroxyethyl cellulose.
17. A gel of claim 15, wherein the polymer is hydroxypropylmethyl cellulose.
18. A gel of claim 15, wherein the polymer is methyl cellulose.
19. A gel of claim 15, wherein the polymer is agarose.
20. A gel of claim 15, wherein the polymer is hydroxyethyl agarose.
21. A gel of claim 15, wherein the polymer is galactomannan.
22. A gel of claim 15, wherein the polymer is dextran.
23. A gel as claimed in claim 15 wherein said preformed polymer has a polydispersity, and wherein said polymer has been subjected to fractionation under conditions sufficient to reduce the polydispersity thereof.
24. A gel of claim 23, wherein the fractionation method is gel filtration.
25. A gel of claim 23, wherein the polymer is hydroxyethyl cellulose.
26. A gel of claim 1 containing more than one polymer.
27. A gel of claim 26, wherein the polymers are hydroxyethyl cellulose and hydroxyethyl agarose.
28. A gel of claim 1 containing a synthetic polymer.
29. A gel of claim 28, wherein the polymer is polyacrylamide.
30. A gel of claim 28, wherein the polymer is poly-N-acryloyl-tris(hydroxymethyl)-aminomethane.
31. A method for preparing a gel suited for use in electrophoretic separation of high molecular weight molecules comprising the steps of:
    dissolving so much of at least one monomer, at least one vinyl cross linker, and at least one preformed polymer in a mutual solvent such that the concentration of said preformed polymer is about 0.005 to 2% (w/v) and the concentration of a combination of said monomer plus said cross linker is at least about 4% (w/v), wherein said monomer and cross linker contain vinyl groups, provided that when said monomer is acrylamide, and said cross linker is N,N'-methylene-bis-acrylamide, said polymer is not agarose; and
    free radical polymerizing and cross linking said monomer and said cross linker in said solution through said vinyl groups sufficient to form a gel;
    wherein said polymerization is carried out under conditions sufficient to form a gel which selectively retards the electrophoretic migration rate of larger macro molecules, as compared to the migration rate of smaller macro molecules, from among DNA fragments of about 100 bp to 3,000 bp, by at least 5 fold as compared to the migration rates of the same molecules under the same conditions in a gel of substantially the same concentration and composition comprising the free radical polymerization reaction product of a solution containing identical concentrations of said monomer and said cross linker but in the absence of said preformed polymer.
32. A method of claim 31, wherein the gel contains one monomer.
33. A method of claim 32, wherein the monomer is N-acryloyl-tris(hydroxymethyl)aminomethane.
34. A method of claim 32, wherein the monomer is acrylamide.
35. A method of claim 32, wherein the monomer is N-acryloyl-1-amino-1-deoxy-D-galactitol.
36. A method of claim 31, wherein the gel contains more than one monomer.
37. A method of claim 36, wherein the monomers are acrylamide and N-acryloyl-tris(hydroxymethyl)aminomethane.
38. A method of claim 31, wherein the gel contains one cross-linker.
39. A method of claim 38, wherein the cross-linker is N,N'-methylene-bis-acrylamide.
40. A method of claim 38, wherein the cross-linker is dihydroxyethylene-bis-acrylamide.
41. A method of claim 38, wherein the cross-linker is piperazine-di-acrylamide.
42. A method of claim 31, wherein the gel contains more than one cross-linker.
43. A method of claim 42, wherein the cross-linkers are N,N'-methylene-bis-acrylamide and dihydroxyethylene-bis-acrylamide.

44. A method of claim 31, wherein the gel contains one polymer.

45. A method of claim 44, wherein the polymer is a polysaccharide.

46. A method of claim 45, wherein the polymer is hydroxyethyl cellulose.

47. A method of claim 45, wherein the polymer is hydroxypropylmethyl cellulose.

48. A method of claim 45, wherein the polymer is methyl cellulose.

49. A method of claim 45, wherein the polymer is agarose.

50. A method of claim 45, wherein the polymer is hydroxyethyl agarose.

51. A method of claim 45, wherein the polymer is galactomannan.

52. A method of claim 45, wherein the polymer is dextran.

53. A method as claimed in claim 45 further including the step of subjecting said preformed polymer to fractionation, prior to combining said preformed polymer with said monomer and said cross linker, under conditions which are sufficient to reduce the polydispersity of said polymer.

54. A method of claim 53, wherein the fractionation method is gel filtration.

55. A method of claim 53, wherein the polymer is hydroxyethyl cellulose.

56. A method of claim 31, wherein the gel contains more than one polymer.

57. A method of claim 56, wherein the polymers are hydroxyethyl cellulose and hydroxyethyl agarose.

58. A method of claim 31, wherein the gel contains a synthetic polymer.

59. A method of claim 58, wherein the polymer is polyacrylamide.

60. A method of claim 58, wherein the polymer is poly-N-acryloyl-tris(hydroxymethyl)aminomethane.

61. A method of electrophoretic separation of large molecules of about the size and charge of DNA molecules which comprises:
    forming a gel comprising the polymerization reaction product of a mixture of:
      at least one monomer; and
      at least one cross linker reactive with said monomer and a polymer of said monomer sufficient to cross link said polymer; and
      at least one preformed polymer;
      wherein the concentration of a combination of said monomer and said cross linker is at least about 4% (w/v), and the concentration of said preformed polymer is about 0.005 to 2% (w/v);
    forming said gel into electrophoretic passageway means;
    disposing a mixture of said molecules at one end of said passageway means; and
    subjecting said mixture of molecules to an electrophoretic current and voltage for a time and at a temperature sufficient to cause said molecules to migrate through said gel a distance which is related to molecular weights of said molecules;
      wherein said gel selectively retards electrophoretic migration rates of larger macro molecules, as compared to migration rates of smaller macro molecules, from among molecules of about 100 bp to 3,000 bp, by at least 5 fold as compared to the migration rates of the same molecules under the same conditions in a gel of substantially the same concentration and composition comprising the free radical polymerization reaction product of said monomer and said cross linker but in the absence of said preformed polymer.

62. An electrophoretic method of claim 61, wherein the gel contains one monomer.

63. An electrophoretic method of claim 62, wherein the monomer is N-acryloyl-tris(hydroxymethyl)aminomethane.

64. An electrophoretic method of claim 62, wherein the monomer is acrylamide.

65. An electrophoretic method gel of claim 62, wherein the monomer is N-acryloyl-1-amino-1-deoxy-D-galactitol.

66. An electrophoretic method of claim 61, wherein the gel contains more than one monomer.

67. An electrophoretic method of claim 66, wherein the monomers are acrylamide and N-acryloyl-tris(hydroxymethyl)aminomethane.

68. An electrophoretic method of claim 61, wherein the gel contains one cross-linker.

69. An electrophoretic method of claim 68, wherein the cross-linker is N,N'-methylene-bisacrylamide.

70. An electrophoretic method of claim 68, wherein the cross-linker is dihydroxyethylene-bisacrylamide.

71. An electrophoretic method of claim 68, wherein the cross-linker is piperazine-diacrylamide.

72. An electrophoretic method of claim 61, wherein the gel contains more than one cross linker.

73. An electrophoretic method of claim 72, wherein the cross-linkers are N,N'-methylene-bisacrylamide and dihydroxyethylene-bis-acrylamide.

74. An electrophoretic method of claim 61, wherein the gel contains one polymer.

75. An electrophoretic method of claim 74, wherein the polymer is a polysaccharide.

76. An electrophoretic method of claim 75, wherein the polymer is hydroxyethyl cellulose.

77. An electrophoretic method of claim 75, wherein the polymer is hydroxypropylmethyl cellulose.

78. An electrophoretic method of claim 75, wherein the polymer is methyl cellulose.

79. An electrophoretic method of claim 75, wherein the polymer is agarose.

80. An electrophoretic method of claim 75, wherein the polymer is hydroxyethyl agarose.

81. An electrophoretic method of claim 75, wherein the polymer is galactomannan.

82. An electrophoretic method of claim 75, wherein the polymer is dextran.

83. The electrophoretic method as claimed in claim 61 wherein said preformed polymer has been subjected to fractionation under conditions sufficient to reduce the polydispersity of said polymer before it is admixed with said monomer and said cross linker.

84. An electrophoretic method of claim 83, wherein the fractionation method is gel filtration.

85. An electrophoretic method of claim 83, wherein the polymer is hydroxyethyl cellulose.

86. An electrophoretic method of claim 61, wherein the gel contains more than one polymer.

87. An electrophoretic method of claim 86, wherein the polymers are hydroxyethyl cellulose and hydroxyethyl agarose.

88. An electrophoretic method of claim 61, wherein the gel contains a synthetic polymer.

89. An electrophoretic method of claim 88, wherein the polymer is polyacrylamide.

90. An electrophoretic method of claim 88, wherein the polymer is poly-N-acryloyl-tris(hydroxymethyl) aminomethane.

* * * * *